US010420903B2

(12) United States Patent
Chen et al.

(10) Patent No.: US 10,420,903 B2
(45) Date of Patent: Sep. 24, 2019

(54) AEROSOL GENERATING APPARATUS WITH INTERCHANGEABLE PARTS

(71) Applicant: MicroBase Technology Corp., Taoyuan (TW)

(72) Inventors: Po-Chuan Chen, Taoyuan (TW); Yi-Tong Chen, Taoyuan (TW); Sheng-Kai Lin, Taoyuan (TW); Ting-Kai Tsai, Taoyuan (TW); Laurence Kao, New York, NY (US)

(73) Assignee: MicroBase Technology Corp., Taoyuan (TW)

( * ) Notice: Subject to any disclaimer, the term of this patent is extended or adjusted under 35 U.S.C. 154(b) by 86 days.

(21) Appl. No.: 15/323,972

(22) PCT Filed: Feb. 15, 2016

(86) PCT No.: PCT/US2016/017984

§ 371 (c)(1),
(2) Date: Jan. 5, 2017

(87) PCT Pub. No.: WO2016/133856

PCT Pub. Date: Aug. 25, 2016

(65) Prior Publication Data

US 2017/0203055 A1 Jul. 20, 2017

Related U.S. Application Data

(60) Provisional application No. 62/116,572, filed on Feb. 16, 2015.

(51) Int. Cl.
*A61M 11/00* (2006.01)
*A61M 15/00* (2006.01)
(Continued)

(52) U.S. Cl.
CPC .......... *A61M 11/005* (2013.01); *A61M 15/00* (2013.01); *B05B 17/0646* (2013.01);
(Continued)

(58) Field of Classification Search
CPC ................ A61M 11/005; A61M 15/00; A61M 2205/123; B05B 17/06
See application file for complete search history.

(56) References Cited

U.S. PATENT DOCUMENTS

2005/0034719 A1 2/2005 Feiner et al.
2009/0137950 A1 5/2009 Loeber et al.
(Continued)

FOREIGN PATENT DOCUMENTS

EP 1762264 A1 3/2007
WO WO2013161986 A1 10/2013
(Continued)

OTHER PUBLICATIONS

Lee W. Young, The internationl search report and the written opinion of the Internaional Search Authority, dated Aug. 29, 2016, whole codument, USPTO as ISA.
(Continued)

*Primary Examiner* — Peter S Vasat
(74) *Attorney, Agent, or Firm* — Opes IP Consulting Co. Ltd

(57) ABSTRACT

An aerosol generating apparatus with interchangeable parts is disclosed. The aerosol generating apparatus includes a holder for accommodating a structure plate and an oscillation generator. The structure plate includes an inlet surface, an outlet surface, a projection extending from the face of the inlet surface, and a through hole. The through hole penetrates the structure plate. The oscillation generator is coupled with and vibrates the structure plate. A reservoir for providing a liquid medicament is also disclosed. The reser-
(Continued)

voir is detachably engaged with the holder and includes a membrane with a plurality of orifices. During aerosolization, the liquid medicament passes through the plurality of orifices. When the reservoir is engaged with the holder, the membrane of the reservoir is in contact with the projection extending from the face of the inlet surface. In addition, the oscillation generator vibrates the membrane through the projection on the inlet surface. As such, the liquid medicament aerosolizes and ejects via the outlet surface of the structure plate.

19 Claims, 21 Drawing Sheets

(51) Int. Cl.
*B05B 17/00* (2006.01)
*B05B 17/06* (2006.01)

(52) U.S. Cl.
CPC ... *B05B 17/0653* (2013.01); *A61M 2205/121* (2013.01); *A61M 2205/123* (2013.01); *A61M 2205/6045* (2013.01)

(56) References Cited

U.S. PATENT DOCUMENTS

2013/0074832 A1 3/2013 Gallem et al.
2013/0119151 A1* 5/2013 Moran ................. A61M 11/005 239/102.2
2013/0126637 A1 5/2013 Hsieh et al.
2013/0299607 A1* 11/2013 Wilkerson .......... B05B 17/0646 239/328
2014/0116426 A1 5/2014 Mullinger et al.
2016/0158789 A1* 6/2016 Selby ................... A61M 11/005 239/102.1

FOREIGN PATENT DOCUMENTS

WO WO2015004449 1/2015
WO WO 2015004449 A1 * 1/2015 ......... B05B 17/0646

OTHER PUBLICATIONS

Examiner's Report issued by Canadian Patent Office, dated Feb. 8, 2018.
Extended European search report, dated Apr. 10, 2018.

* cited by examiner

| | Aerosolization Efficiency(ml/min) | |
|---|---|---|
| Diameter of Through Hole(mm) | Height H<0.1mm | Height H>0.1mm(e.g.,0.2mm) |
| 1.9 | 0.02 | 0.3 |
| 2 | 0.02 | 0.3 |
| 2.1 | 0.02 | 0.3 |
| 2.2 | 0.07 | 0.33 |
| 2.3 | 0.06 | 0.36 |
| 2.4 | 0.07 | 0.45 |
| 2.5 | 0.05 | 0.38 |
| 2.6 | 0.07 | 0.58 |
| 2.7 | 0.08 | 0.3 |
| 2.8 | 0.04 | 0.5 |
| 2.9 | 0.04 | 0.54 |
| 3 | 0.06 | 0.22 |

AEROSOL GENERATING APPARATUS WITH INTERCHANGEABLE PARTS

CROSS REFERENCE TO RELATED APPLICATION

This U.S. National Stage claims priority to PCT Application PCT/US2016/017984 filed on Feb. 15, 2016, which claims priority to U.S. Provisional Application Ser. No. 62/116,572 filed on Feb. 16, 2015. The entire content of each off the above-identified priority applications is incorporated herein by reference.

FIELD

The present disclosure relates to an aerosol generating apparatus and more particularly to an aerosol generating apparatus with interchangeable parts.

BACKGROUND

An aerosol generating apparatus, also called a nebulizer, generates aerosols or tiny droplets. A nebulizer's typical use is to generate aerosol of liquid medicament for patients to inhale in order to cure pulmonary or other diseases. Ordinarily, a fixed amount of liquid medicament is provided to a perforated membrane, which is vibrated by oscillation generators such that the liquid passes through the membrane and is aerosolized. There are many ways to generate oscillation and in modern days people use piezoelectric (PZT) materials. When the piezoelectric material receives power, it vibrates and the resulting energy is transmitted to the membrane to aerosolize the liquid provided thereto.

Aerosol generating apparatuses can be costly due to the liquid medicament therein and the sophisticated components required for efficient and accurate aerosolization. Operation of aerosol generating apparatuses can also be complicated. For example, failure to timely stop aerosolization leads to overdose and waste. In another example, the oscillation generator can be damaged before the liquid medicament is depleted, requiring the user to replace the entire aerosol generating apparatus. In yet another example, the source for providing liquid medicament may be contaminated before depletion, and the user is again forced to replace the entire aerosol generating apparatus with a new one.

Therefore, there is a need to develop a novel aerosol generating apparatus with interchangeable parts such that faulty components can be replaced to extend the service life of the apparatus.

SUMMARY

In one embodiment, an aerosol generating apparatus including a holder and a reservoir detachably engaged with the holder is disclosed. The holder is configured to accommodate a structure plate and an oscillation generator, and the reservoir includes a membrane. The structure plate includes an inlet surface and an outlet surface opposite to the inlet surface. The inlet surface further includes a projection extending from its face, and a through hole is configured to penetrate the structure plate. The oscillation generator couples with and vibrates the structure plate. The reservoir holds a liquid medicament therein and provides such medicament to the aerosol generating apparatus for aerosolization. The reservoir is detachably engaged with the holder and includes a membrane with a plurality of orifices. During aerosolization, the liquid medicament passes through the orifices and becomes aerosol for patients to breathe in. Particularly, when the reservoir is engaged with the holder, the membrane of the reservoir is in contact with the projection extending from the face of the inlet surface. The oscillation generator is configured to vibrate the membrane through the projection on the inlet surface. As a result, the liquid medicament aerosolizes and ejects via the outlet surface of the structure plate.

In one embodiment, when the reservoir is engaged with the holder, the projection extending from the face of the inlet surface pushes the membrane inward for a distance. The distance is less or equal to the height of the projection.

In one embodiment, the aerosol generating apparatus further includes a gear such that the distance in which the projection pushes the membrane inward can be adjusted when the reservoir is engaged with the holder.

In one embodiment, a space is formed between the inlet surface and the membrane when the projection pushes the membrane inward. In another embodiment, the structure plate further includes a planar part at the inlet surface extending annularly from the projection, and the space between the membrane and the structure plate corresponds to the planar part.

In one embodiment, the reservoir can be removed from the holder and replaced by another reservoir after an aerosolization cycle. As such, the holder, the structure plate and the oscillation generator can be used repeatedly, and the reservoir is disposable.

In one embodiment, the structure plate further includes a planar part at the inlet surface extending annularly from the projection. When the reservoir is engaged with the holder, vibration of the membrane is not affected by the planar part.

In one embodiment, there is no adhesion between the structure plate and the membrane.

In one embodiment, at least one of the holder and the reservoir includes a locking means capable of repeated engagement and release. As such, the reservoir is interchangeable and disposable.

In one embodiment, when the reservoir is engaged with the holder, the plurality of orifices is aligned with a center of the projection extending from the face of the inlet surface.

In one embodiment, the membrane is in direct contact with the projection extending from the face of the inlet surface when the reservoir is engaged with the holder.

In one embodiment, the projection further includes a working surface, dimension of which is not larger than that of the membrane. The working surface is configured to face the membrane. Furthermore, the working surface serves as a primary interface for vibrating the membrane when the projection is in contact with the membrane during aerosolization.

In one embodiment, the structure plate further includes a planar part at the inlet surface extending annularly from the projection. When the reservoir is engaged with the holder, the planar part is not sealed by the membrane.

In one embodiment, the membrane is made of a macromolecular polymer selected from the collection of polyimide, polyethylene (PE), polypropylene (PP) and polyether ether ketone (PEEK). The structure plate and projection are made of metal.

In one embodiment, the projection is circular or of a polygonal shape with three or more edges.

In one embodiment, the aerosol generating apparatus further includes a housing to accommodate the holder. The housing further serves to receive the reservoir.

In one embodiment, the membrane is integrally formed with the reservoir.

In one embodiment, the oscillation generator couples to the outlet surface side of the structure plate.

In one embodiment, the height of the projection is no less than 0.1 mm.

In one embodiment, the through hole at the structure plate widens in the direction from the inlet surface to the outlet surface.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

Figure 1A:
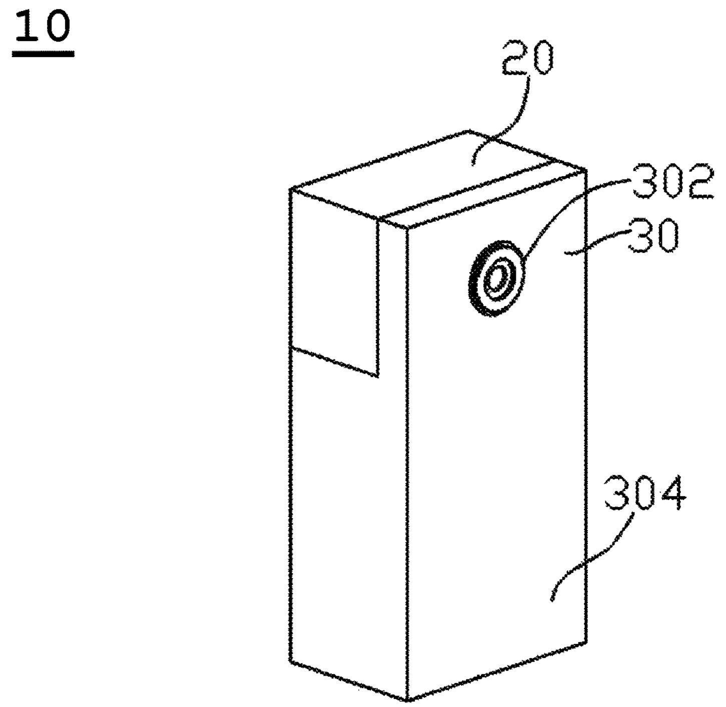
FIGS. 1A-1C are side views of an aerosol generating apparatus with interchangeable parts in accordance with some embodiments of the present disclosure.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

It will be understood that elements described as "under" or "below" other elements would then be oriented "over" or "above" the other elements. The exemplary terms "under" or "below" can, therefore, encompass both an orientation of over and under.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1B:
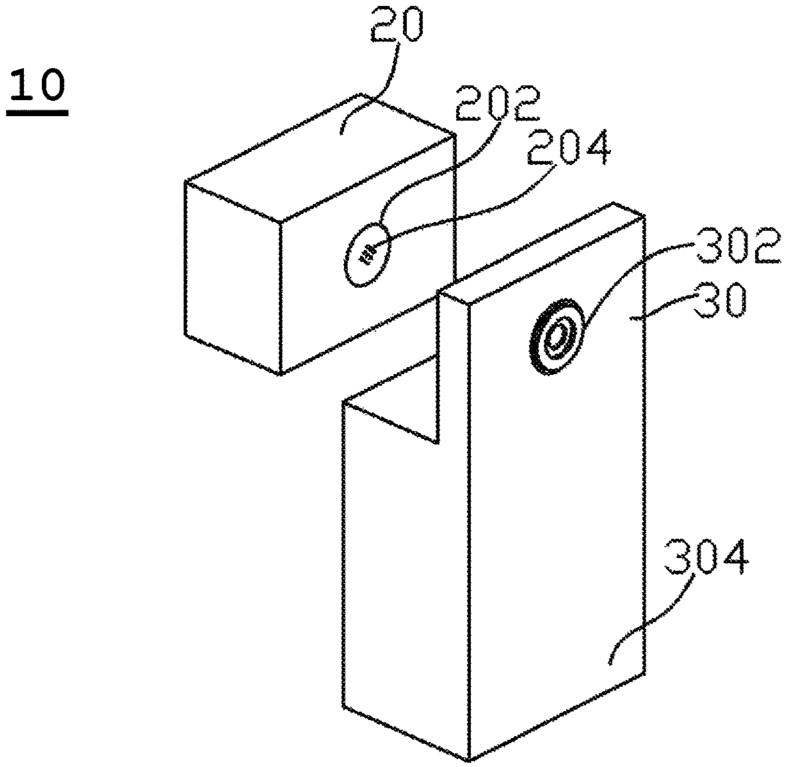
Figure 1C:
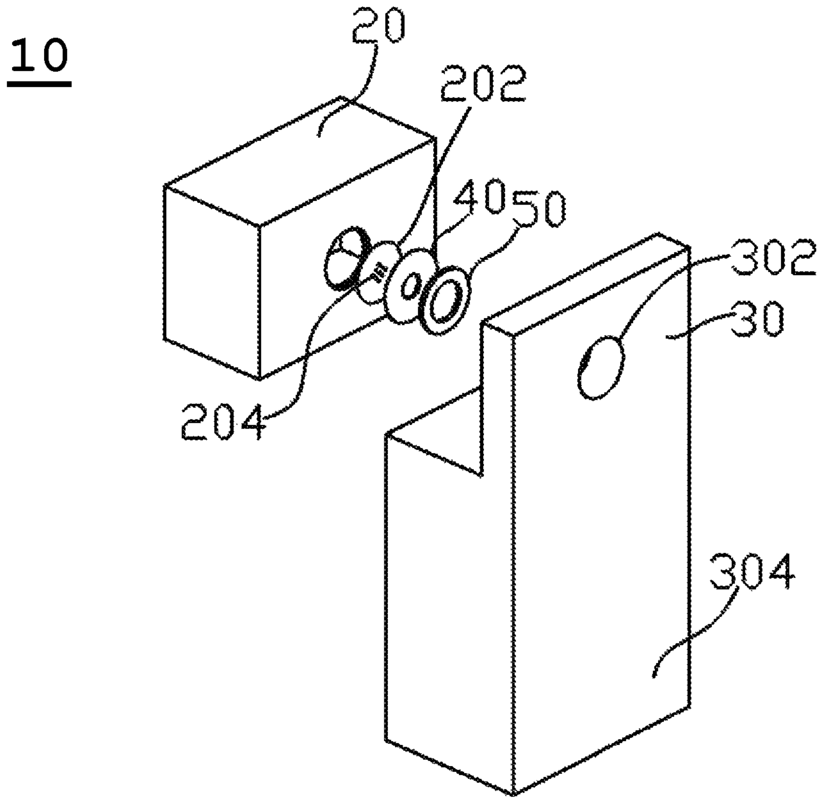

FIGS. 1A-1C are side views of an aerosol generating apparatus with interchangeable parts in accordance with some embodiments of the present disclosure.

Referring to FIG. 1A, an aerosol generating apparatus 10 is disclosed. The aerosol generating apparatus 10 includes a reservoir 20 and a holder 30. Here, the reservoir 20 is engaged with the holder 30 in order to conduct aerosolization. However, the reservoir 20 and the holder 30 are readily detachable from each other, as will be shown by the rest of the embodiments and figures herein. The detachability of the reservoir 20 from the holder 30 allows a user to replace either of such components when needed.

The reservoir 20 is configured to hold a liquid medicament (not shown) to be provided to the aerosol generating apparatus 10 for aerosolization. The relative position between the reservoir 20 and the holder 30 is fixed during aerosolization to ensure the liquid medicament is aerosolized under a controlled manner. The resulting aerosol exits the holder at an opening 302 for patient inhalation. One example of the use of the aerosol generating apparatus 10 is inhalation drug delivery.

In certain embodiments, the aerosol generating apparatus 10 includes a housing 304. The housing 304 may be integrally formed with the holder 30. Alternatively, the housing 304 may be an independent component coupling to or hosting the holder 30. The housing 304 is configured to accommodate the holder 30 and/or to receive the reservoir 20. Additional components of adjustment or security may be added to the holder 30 or the housing 304 to ensure efficient aerosolization. Such additional components will be disclosed in other paragraphs herein.

FIG. 1B illustrates the aerosol generating apparatus 10 with the reservoir 20 disengaged from the holder 30. When the liquid medicament in the reservoir 20 is depleted or that an aerosolization cycle is completed, the user may replace the depleted reservoir 20 with a new one. Alternatively, the reservoir 20 may include an inlet (not shown). Liquid medicament may be refilled into the reservoir 20 such that the reservoir 20 may be used repeatedly. Still, the user may also choose to replace the old reservoir 20 with a new one in other situations, for example, when the liquid medicament is expired. The interchangeable nature of the reservoir 20 makes it disposable, while other components of the aerosol generating apparatus 10 can be used repeatedly. Conversely, if other component of the aerosol generating apparatus 10 is faulty, the reservoir 20 and the liquid medicament therein can be preserved and reused. In another example, if the reservoir 20 is breached and the liquid medicament therein is contaminated, the user may replace the reservoir 20 with a new one. Accordingly, the interchangeable nature of the apparatus 10 helps to reduce waste as it's less costly comparing to replacing the entire apparatus.

In certain embodiments, the reservoir 20 includes a membrane 202, and at least some section of it is porous. That is, the membrane 202 includes a plurality of orifices 204 as outlets for the liquid medicament to eject. Exemplary ways of forming the orifices 204 includes etching or laser drilling. The orifices can be formed by other method known to persons having ordinary skill in the art. The size of the orifices 204 is configured to substantially prevent liquid medicament from leaking. The design of the orifices 204 will be discussed further herein. The membrane 202 is at one side of the reservoir 20 and faces the holder 30, and may be attached to the reservoir 20 by adhesive, sandwiching, soldering and so on. Alternatively, the membrane 202 is integrally formed with the reservoir 20. In some embodiments, the orifices 204 are evenly distributed over the membrane 202. In certain embodiments, the orifices 204 are concentrated at or near the center of the membrane 202. In yet some other embodiments, the orifices 204 are aligned with the opening 302 of the holder 30.

In some embodiments, the membrane 202 is made of a material flexible enough to respond to vibration but sturdy enough to maintain liquid from leakage or prevent contamination from outside environment. In certain embodiments, the membrane 202 is made of a macromolecular polymer of polyimide, polyethylene (PE), polypropylene (PP), polyether ether ketone (PEEK) and/or the combination thereof. When the membrane 202 is integrally formed with the reservoir 20, the two are made of a same material or same combination of materials. A separate container or vial may be added to shield the reservoir 20.

FIG. 1C illustrates a partially exploded view of the aerosol generating apparatus 10. The holder 30 accommodates a structure plate 40 and an oscillation generator 50. The structure plate 40 and the oscillation generator 50 may be coupled by adhesive, welding, bonding, or any measure known to persons having ordinary skill in the art as long as vibration energy can be transmitted therebetween. In some embodiments, the structure plate 40 is positioned between the membrane 202 and the oscillation generator 50 when the reservoir 20 is engaged with the holder 30. The oscillation generator 50 is connected to an electricity source (not shown) and vibrates when it receives electric power. The electric power may be provided by wire or other transmitting means connected to the oscillation generator 50. The electricity source may be disposed at the housing 304. Vibration energy from the oscillation generator 50 is transmitted to the structure plate 40 and then to the membrane 202 during aerosolization. Accordingly, the liquid medicament is aerosolized and exits the aerosol generating apparatus 10 via the opening 302. In certain embodiments, the structure plate 40 is made of metal or any material with rigidity and malleability, and the oscillation generator 50 is a piezo-electric component. For example, the oscillation generator 50 is made of a PZT material.

In some embodiments, the oscillation generator 50 is in the shape of a ring. That is, the oscillation generator 50 includes a through hole at around its center to allow liquid medicament to exit the reservoir 20 through the orifices 204 of the membrane 202. Alternatively, the oscillation generator 50 may be of any shape suitable for transmitting vibration energy. In yet some other embodiments, the oscillation generator 50 may not be a one-piece component. For example, the oscillation generator 50 may be constituted by a few PZT stripes arranged in circle. It is to be noted that the oscillation generator 50 may be of any configuration depending on the need of the specific aerosol generating apparatus 10 and/or the liquid medicament contained therein and thus is not limited to the disclosure herein.

Figure 2A:
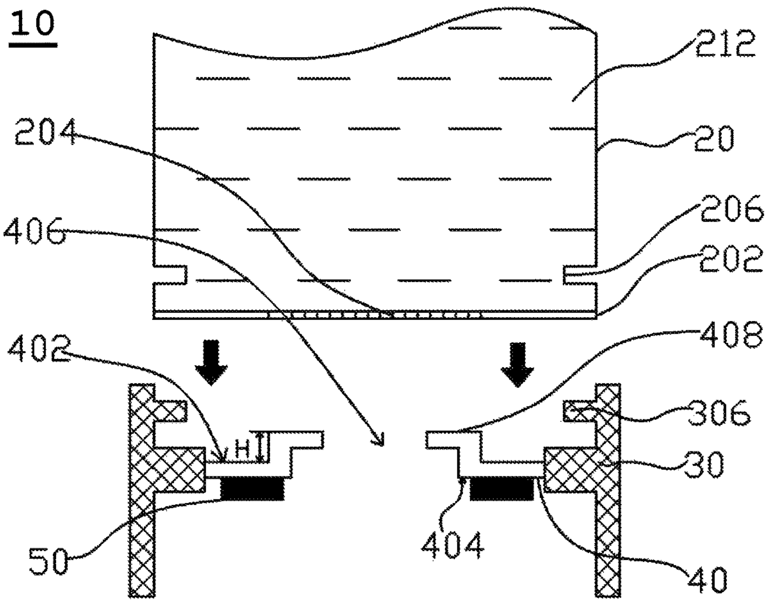
FIGS. 2A and 2B are perspective views of an aerosol generating apparatus with interchangeable parts in accordance with some embodiments of the present disclosure.
Figure 2B:
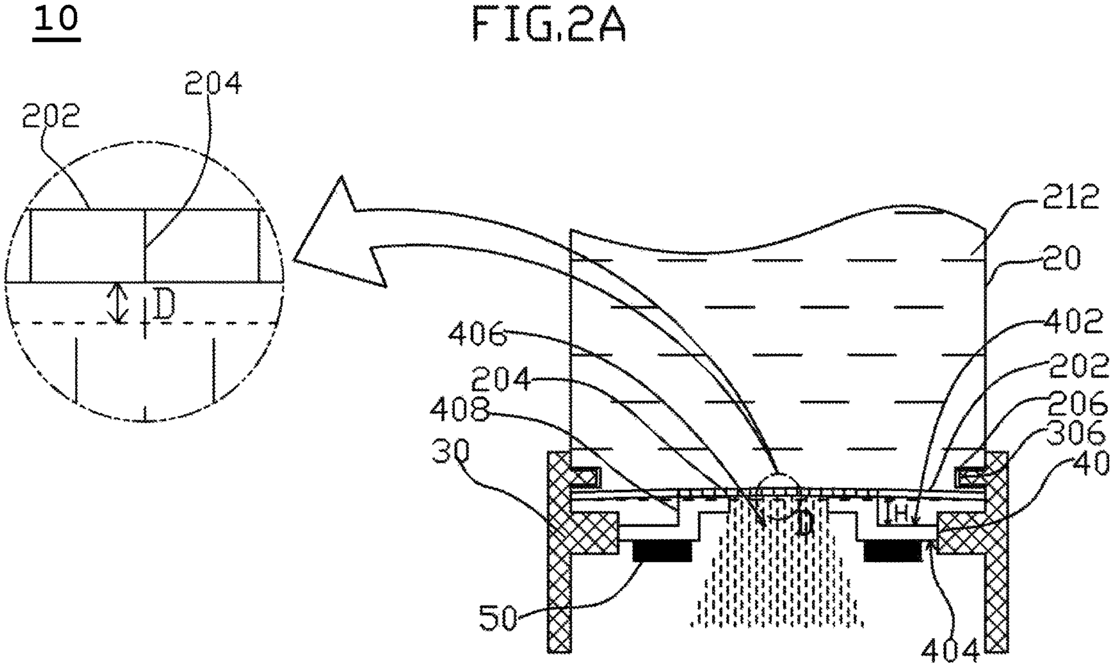

FIGS. 2A and 2B are perspective views of an aerosol generating apparatus with interchangeable parts in accordance with some embodiments of the present disclosure.

FIG. 2A depicts the aerosol generating apparatus 10 in a disengaged state, i.e., the reservoir 20 is not engaged with the holder 30. The reservoir 20 is holding a liquid medicament 212. The membrane 202 is at one side of the reservoir 20, and the plurality of orifices 204 faces an inlet surface 402 of the structure plate 40. Opposite to the inlet surface 402 is an outlet surface 404 of the structure plate. In some embodiments, the outlet surface 404 is not on the opposite side of the inlet surface 402. For example, the two surfaces may be perpendicular to each other. The relative position of the inlet surface 402 and the outlet surface 404 may be arranged as long as the aerosol of the liquid medicament is capable of passing through the structure plate 40 via a through hole 406 penetrating it. In certain embodiments, the through hole 406 is aligned with the opening 302 (not shown here) of the holder 30 for aerosol medicament to exit the aerosol generating apparatus 10.

In certain embodiments, the shape of the through hole 406 may be circular and penetrate the structure plate 40 at about its center. Alternatively, the through hole 406 may be of any shape at any position of the structure plate 40 as long as aerosol medicament is able to pass through and exit the aerosol generating apparatus 10. The definition of the inlet and outlet is from the perspective of the flow of the liquid medicament 212. Ordinarily, the liquid medicament passes through the structure plate 40 from the inlet surface 402 to the outlet surface 404 via the through hole 406. Still, the relative position of the components of the aerosol generating apparatus 10 is not to be limited to the arrangement in the figures as long as the medicament can be aerosolized and ejected.

In some embodiments, the structure plate 40 includes a projection 408 extending from the face of the inlet surface 402 for a height H. Particularly, the height H is measured from the inlet surface 402 to the highest point, e.g., the face or summit, of the projection 408, as depicted in FIG. 2A. The height H may be adjusted depending on the nature or purpose of the aerosol generating apparatus 10 and/or the liquid medicament 212 therein. For example, depending on the material of the membrane 202, the height H may be increased or decreased to reach certain aerosolization efficiency. In a preferred embodiment, the height H is no less than 0.1 mm. Further details will be discussed herein. In certain embodiments, the projection 408 is formed by stamping the structure plate 40, thereby making the projection 408 integrally formed with the structure plate 40. Alternatively, the projection 408 is individually manufactured and adhered to the structure plate 40. The projection 408 and the structure plate 40 may be made of different materials.

In certain embodiments, at least one of the reservoir 20 and the holder 30 includes a locking means capable of repeated engagement and release. One example, as shown in FIGS. 2A and 2B, is that the reservoir 20 includes a first mating part 206 such as a groove, and the holder includes a second mating part 306 such as a rib. When the reservoir 20 is engaged with the holder 30, the first and second parts 206, 306 ensure that the relative position of the two is fixed during aerosolization. The material and arrangement of the first and second parts 206, 306 are that the user can disengage the reservoir 20 from the holder 30 without breaking either of them. Accordingly, the reservoir 20 and the holder 30 can be interchanged and used repeatedly. In one example, when the liquid medicament 212 in the reservoir 20 is depleted, the user can replace it with a new reservoir 20 for the next aerosolization cycle.

FIG. 2B depicts the aerosol generating apparatus 10 in an engaged state, i.e., the reservoir 20 is engaged with the holder 30. The aerosol generating apparatus 10 is ready to generate aerosol in the engaged state. Particularly, when engaged, the membrane 202 of the reservoir 20 is in contact with the projection 408, which extends from the face of the inlet surface 402. In some embodiments, the projection 408 not only is in contact with the membrane 202 but also pushes the membrane 202 inward into the reservoir 20 for a distance D. The distance D is measured from the upper surface of the membrane 202 to its lowest point of the indention. In a preferred embodiment, the distance D is less than the height H, thereby not the entire projection 408 is pushed against the membrane 202. In other embodiments, the distance D is equal to the height H, thereby the entire projection 408 is pushed against the membrane 202. In some other embodiments, the distance D is zero, thereby the membrane 202 is only in contact with but not pushed inward by the projection 408. In any case, the projection 408 serves as the interface of vibration energy transmission between the oscillation generator 50 and the membrane 202 and the oscillation amplitude is the highest at around the center of the membrane 202. Furthermore, those sections of the membrane 202 not in contact with the projection 408 are in free-form, vibration of which is not affected by the projection 408 or the structure plate 40. As such, the membrane 202 is capable of reaching a resonance state with the frequency applied to the aerosol generating apparatus 10 or generated by the oscillation generator 50 to help improve aerosolization efficiency and prevent energy waste.

In some embodiments, only such section of the membrane 202 having orifices 204 is in contact with and/or pushed inward by the projection 408 in the engaged state, as shown in FIG. 2B. The plurality of orifices 204 are aligned with the projection 408 and/or the through hole 406 such that the liquid medicament can exit the reservoir 20 to the holder 30 during aerosolization. Alternatively, the plurality of orifices 204 are aligned with the center of the projection 408. It is to be noted, as it's also shown in the figures throughout this disclosure, that the distribution of the orifices 204 is not required to be in the proximity of the through hole 406 and/or the projection 408. The orifices 204 may be distributed over the entire membrane 202 if needed.

In certain embodiments, due to the engagement of the reservoir 20 with the holder 30, the membrane 202 is pushed inward by the projection 408 and thus a distance D is formed. As such, stress concentration point(s) is created in proximity to where the projection 408 contacts with the membrane 202. In certain embodiments, when electric power is provided to the oscillation generator 50, a majority of the energy is transmitted from the structure plate 40 to vibrate the membrane 202 through the stress concentration point(s) of the projection 408. As a result, the liquid medicament 212 aerosolizes and ejects via the outlet surface 404 of the structure plate 40. The formation of the stress concentration point(s) helps the membrane 202 to achieve a resonance state and thus improve aerosolization efficiency.

In certain embodiments, there is no adhesion between the membrane 202 and the structure plate 40 or between the membrane 202 and the projection 408. The foregoing configuration ensures that the reservoir 20 is detachable from the holder 30 without damaging any component of the aerosol generating apparatus 10. As such, either the reservoir 20 or the holder 30 (and the structure plate 40 and oscillation generator 50 it accommodates) is interchangeable and disposable. User can discard a depleted reservoir 20 or a faulty holder 30 or any other interchangeable components. Still, an interface, such as a protection layer or coating, may be provided between the membrane 202 and the structure plate 40 and the projection 408 thereof as long as the existence of the interface would not impede the detachability between the reservoir 20 and the holder 30.

In some embodiments, the through hole 406 widens in the direction from the inlet surface 402 to the outlet surface 404. Such configuration reduces obstruction to the aerosol exiting the aerosol generating apparatus 10. In certain embodiments, the through hole 406 may widen continuously to as far as the outlet surface 404. Alternatively, the through hole 406 may not widen continuously. For example, the through hole 406 may have a perpendicular wall and then a outwardly widening wall. In yet some other embodiments, there is a stepped structure at the through hole 406. With reference to FIG. 2B, the stepped structure of the through hole 406 may be formed by the projection 408 and the outlet surface 404, and may extend to the oscillation generator 50. Ideally, the shape of through hole 406 shall not narrow in the direction from the inlet surface 402 to the outlet surface 404 so as to obstruct the aerosol exiting the aerosol generating apparatus 10.

Referring to FIGS. 2A and 2B, it is to be noted that in the present disclosure, the term "engaged state" shall mean that the reservoir 20 is coupled with the holder 30. More particularly, in the engaged state, the membrane 202 is in contact or pushed inward by the projection 408. The term "disengaged state" shall mean that the reservoir 20 is separated from the holder 30. More particularly, in the disengaged state, the membrane 202 is not in contact with the projection 408.

FIGS. 3A-3E are partial views of an aerosol generating apparatus with interchangeable parts in accordance with some embodiments of the present disclosure.

Figure 3A:
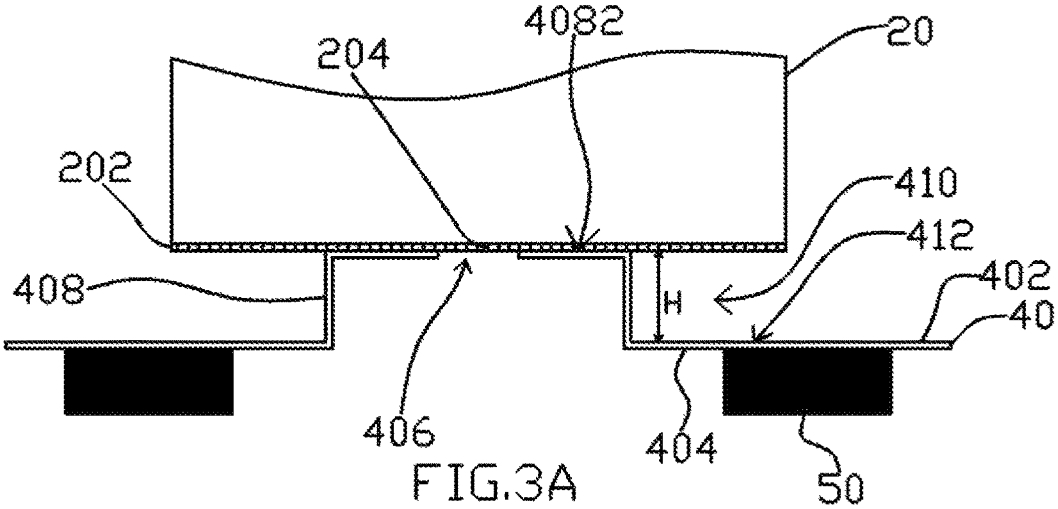
FIGS. 3A-3E are partial views of an aerosol generating apparatus with interchangeable parts in accordance with some embodiments of the present disclosure.

FIG. 3A is a partial view of the aerosol generating apparatus 10 in the engaged state. The membrane 202 is in direct contact with but not pushed inward by the projection 408 extending from the face of the inlet surface 402 of the structure plate 40. Thus, the interface between the membrane 202 and the top surface of the projection 408 is substantially leveled. Alternatively, an additional layer, such as a protection layer or a coating, may be provided between the membrane 202 and the projection 408. Still, as long as neither the transmission of vibration energy from the projection 408 to the membrane 202 nor the detachability of the projection 408 and the membrane 202 is affected, any layer may be added between the projection and the membrane and the two should still be considered as in direct contact.

In some embodiments, the projection 408 includes a top surface facing the membrane 202 when engaged, and the section of such top surface in contact with the membrane 202 is the working surface 4082. In FIG. 3A, the working surface 4082 is the same size as the top surface of the projection 408. The working surface 4082 serves as the interface for transmitting the vibration energy from the oscillation generator 50 to the membrane 202 for aerosolization. As shown in FIGS. 3A-3E, the dimension, i.e., area, of the working surface 4082 is subject to change. The factors affecting its dimension may include size of the projection or the membrane, shape of the working surface, shape of the projection, extent of the membrane being pushed inward by the projection, material of the membrane, and so on. The dimension of the working surface 4082 may also be adjusted according to the purpose of the aerosol generating apparatus or the liquid medicament contained therein. In a preferred embodiment, the dimension of the working surface 4082 is not larger than that of the membrane 202 to ensure desired aerosolization efficiency.

In some embodiments, when the membrane 202 is in contact with the projection 408, a space 410 is formed between the membrane 202 and the inlet surface 402. The space 410 is preserved because not the entire membrane 202 is in contact with the projection 408. As vibration energy is transmitted from the oscillation generator 50 to the membrane 202 through the working surface 4082, those sections of the membrane 202 not in touch with or affected by the projection 408 are in free-form. Here, being in "free-form" or "free-form movement" means that the vibration of the membrane 202 is not affected by undesirable influences of surrounding component(s) or structure(s) of the aerosol generating apparatus. In addition "free-form" or "free-form movement" means that the membrane 202 is capable of reaching a resonance state corresponding to the vibration energy received from the projection 408. Hence, although certain section of the membrane 202 is in contact with and influenced by the projection 408, the membrane 202 is in "free-form" or "free-form movement" as long as it's capable of resonating. The formation of the space 410 helps to preserve the free-form movement of the membrane 202. As such, aerosolization efficiency is improved because energy from the oscillation generator 50 is more effectively transmitted to the membrane 202 for vibration.

In certain embodiments, the structure plate 40 includes a planar part 412 at the inlet surface 402, and the planar part 412 extends annually from the projection 408. As depicted in FIG. 3A, the space 410 substantially corresponds to the planar part 412. Accordingly, the planar part 412 is not in contact with the membrane 202 in the engaged state such that those parts of the membrane 202 corresponding to the planar part 412 is in free-form and the vibration thereof is not affected by the planar part 412 of the structure plate 40. In other words, the planar part 412 is neither sealed by the membrane 202, nor isolated from the interior environment of the aerosol generating apparatus 10 by the membrane 202 in the engaged state. Furthermore, the sidewall of the projection 408 is not isolated from the interior environment of the aerosol generating apparatus in the engaged state. The foregoing also ensures that the membrane 202 is capable of free-form movement in the engaged state.

Figure 3B:
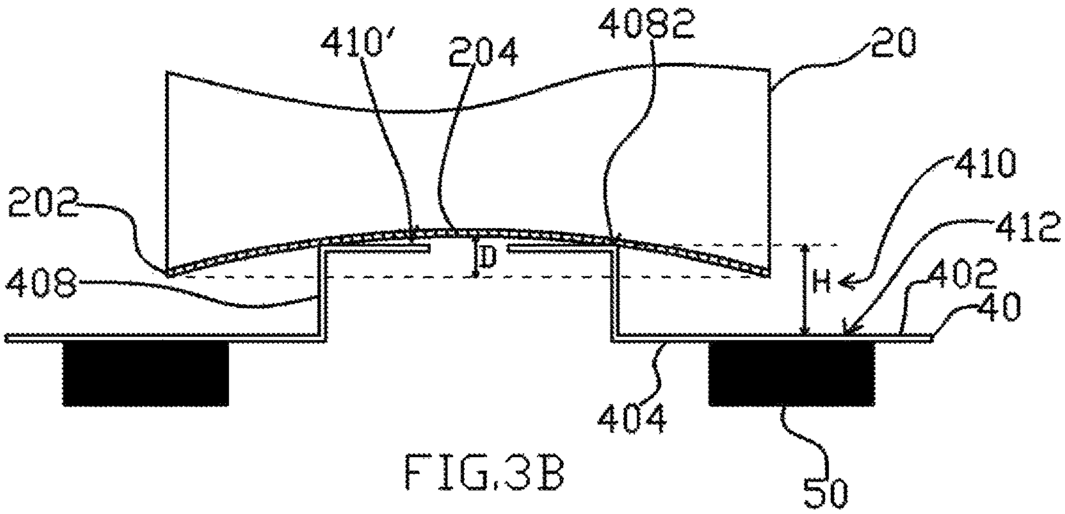

FIG. 3B is a partial view of the aerosol generating apparatus 10 in an engaged state. Here, the projection 408 pushes the membrane 202 inward. In some embodiments, a space 410' may be formed between the upper surface of the projection 408 and the membrane 202. As such, the dimension of the working surface 4082 of the projection 408 is reduced because its area of contact with the membrane 202 is reduced. Still, as long as there is some working surface 4028 and vibration energy can be transmitted from the projection 408 to the membrane 202, such configuration is within the scope of the present disclosure. In some embodiments, the distance D is less than the height H because not the entire projection 408 is pushed inward against the membrane 202. Thus, sections of the membrane 202 other than those in contact with the projection 408 are in free from and vibration of which is not affected by the projection 408 or the structure plate 40. In certain embodiments, the distance D can be adjusted pursuant to the need of the aerosol generating apparatus and the particle size of the liquid medicament.

In certain embodiments, the height H of the projection 408 is no less than 0.1 mm in order to preserve the space 410 and the free-form movement of those sections not in contact with the structure plate 40 and/or the projection 408. In other embodiments, the distance D is less than the height H to ensure that less than the entire projection 408 is pushed inward against membrane 202. The benefits of the foregoing arrangement have been discussed in preceding paragraph and will not be repeated.

Figure 3C:
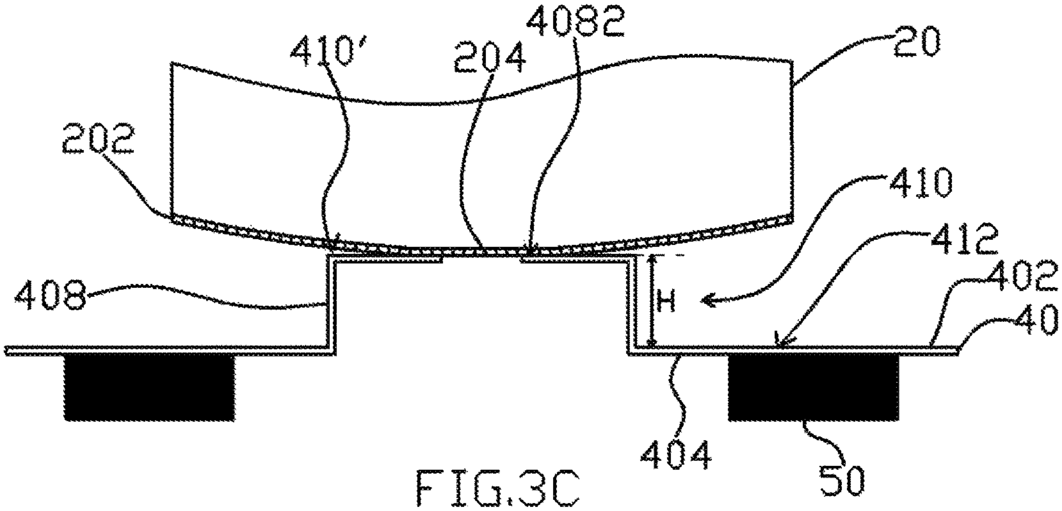

FIG. 3C is a partial view of the aerosol generating apparatus 10 in an engaged state. Here, the membrane 202 is in a substantially convex shape and is merely in contact with the projection 408 such that no distance D is formed. In other words, the membrane 202 is not pushed inward by the projection 408. As previously disclosed, as long as the membrane 202 is in contact with the projection 408 such that vibration energy can be transmitted, the aerosol generating apparatus 10 of the present disclosure is workable. Particularly, comparing to FIG. 3B, the working surface 4082 in FIG. 3C is located closer to the center of the projection 408 and a space 410' is formed between the membrane 202 and the projection 408 at their exterior perimeter. Nevertheless, the space 410 is still formed in correspondence to the planar part 412 to ensure free-form movement of the membrane 202. As such, in the engaged state, as long as the membrane 202 is at least partially in contact the projection 408, vibration energy can still be transmitted via the projection 408 to the membrane 202 for aerosolization. Such vibration energy causes the free-form movement of the sections of the membrane 202 not in contact with and thus not affected by the structure plate 40 and/or the projection 408 so as to achieve a desired aerosolization.

Figure 3D:
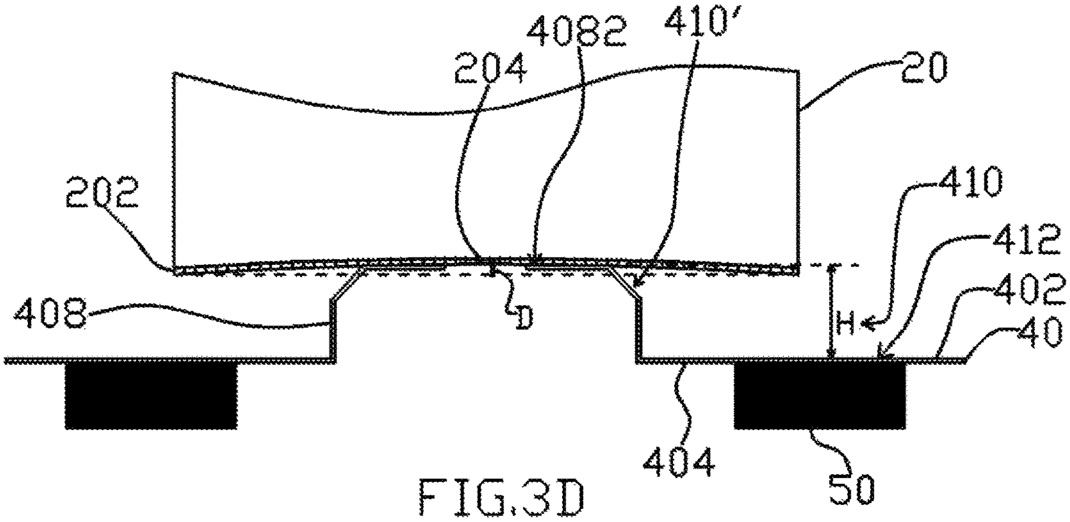

FIG. 3D is a partial view of the aerosol generating apparatus 10 in an engaged state. Here, the projection 408 has a slope at its exterior perimeter such that the space 410' is formed when the membrane 202 is in contact and pushed inward by the projection 408. The slope may be formed during the manufacturing process of the projection 408 and its level of inclination may vary, depending on the desired amount of space 410'. The space 410' renders that only certain sections of the membrane 202 are in contact with the projection 408, i.e., at the working surface 4082. As such, the amount of vibration energy transmitted to the membrane 202 can be adjusted by the exterior shape of the projection 408 in order to achieve a desired aerosolization efficiency. Similar to the preceding disclosure, the membrane 202 is capable of free-form movement due to the formation of the space 410.

Figure 3E:
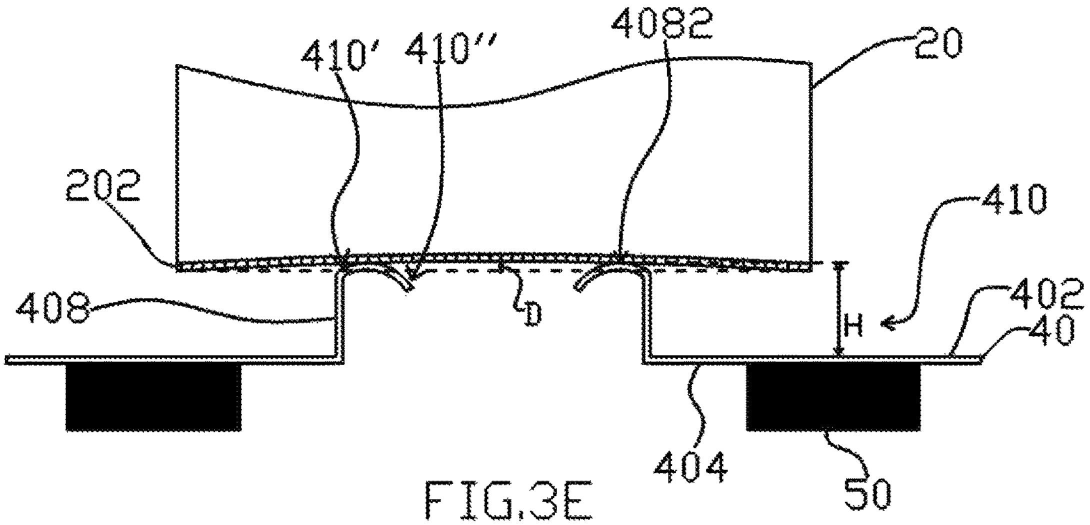

FIG. 3E is a partial view of the aerosol generating apparatus 10 in an engaged state. Here, the projection 408 is inclined at both of its interior and exterior perimeters. As such, spaces 410' and 410" are formed, and the size of the working surface 4082 is further adjusted. Similar to the preceding disclosure, the configuration here is capable of controlling the amount of vibration energy transmitted to the membrane 202 while at least some section of the membrane 202 is in free-form and its vibration is not affected by the structure plate 40.

According to FIGS. 3A to 3E, the design of the projection 408 can be adjusted as long as some part of the membrane 202 is in contact with and/or pushed inward by the projection 408. As such, vibration energy can be transmitted to the membrane 202 via the interface, i.e., the working surface 4082. Particularly, some space 410 is formed between the membrane 202 and the structure plate 40 such that those sections of the membrane 202 not in contact with the projection 408 enjoy free-form movement without being affected by the structure plate 40. Moreover, In certain embodiments, the membrane 202 is pushed inward by the projection by a distance D, and the distance D is less than or at most equal to the height H of the projection 408. The pushing of the projection 408 against membrane 202 creates stress concentration points such that aerosolization efficiency is improved. Details of the foregoing will be further discussed herein.

Figure 4A:
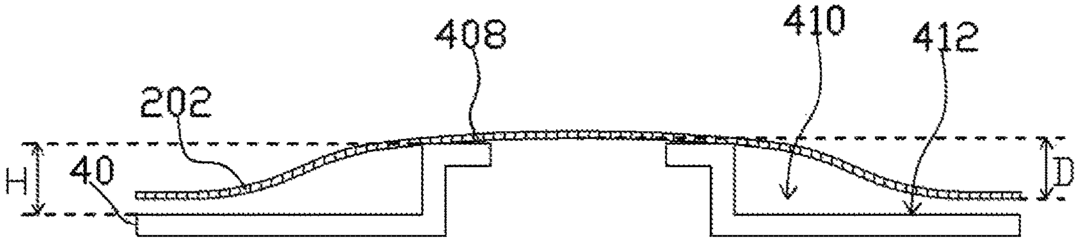
FIGS. 4A and 4B are partial views of an aerosol generating apparatus with interchangeable parts in accordance with some embodiments of the present disclosure.
Figure 4B:
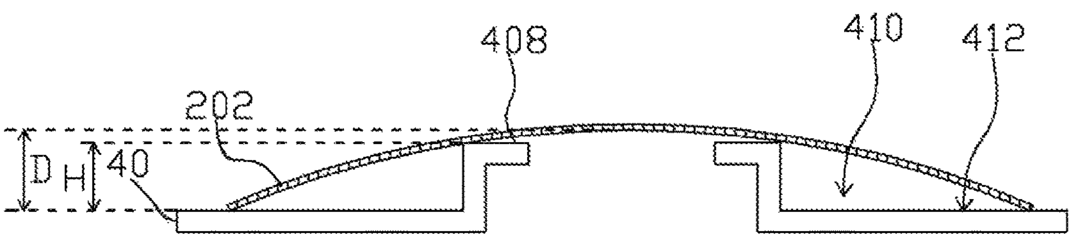

FIGS. 4A and 4B are partial views of an aerosol generating apparatus with interchangeable parts in accordance with some embodiments of the present disclosure.

In FIG. 4A, only the membrane 202 and the structure plate 40 is depicted. A portion of the membrane 202 is contact with the projection 408 and space 410 is formed between the structure plate 40 and the membrane 202. The space 410 extends to the exterior perimeter of the structure plate 40. In other words, the membrane 202 is only in contact with the projection 408 but not with the exterior perimeter of the structure plate 40. As a result, such sections of the membrane 202 not in contact with the structure plate 40 or the projection 408 are in free-form.

On the other hand, in FIG. 4B, the vibration of the membrane 202 is affected by the structure plate 40. Here, the membrane 202 is pushed inward by the projection 408 to the extent that the distance D is greater than the height H. As a result, although space 410 is still formed, the membrane 202 and the structure plate 40 are in contact with each other at the exterior perimeters. In addition, the planar par 412 becomes sealed by the membrane 202 as the space 410 is confined. In other words, the planar part 412 is not in air communication with the interior environment of the aerosol generating apparatus 10. In the present disclosure, the distance D should not be greater than the height H to prevent the structure plate 40 affecting or hindering the vibration of the membrane 202.

FIGS. 5A to 5H are perspective views of an aerosol generating apparatus with interchangeable parts in accordance with some embodiments of the present disclosure.

Figure 5A:
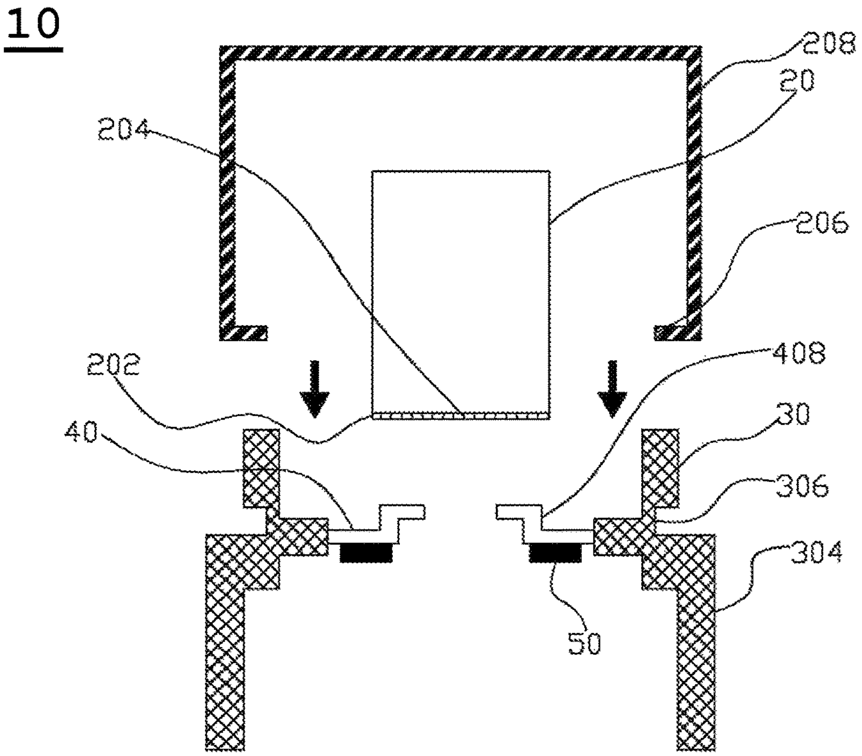
FIGS. 5A to 5H are perspective views of an aerosol generating apparatus with interchangeable parts in accordance with some embodiments of the present disclosure.
Figure 5B:
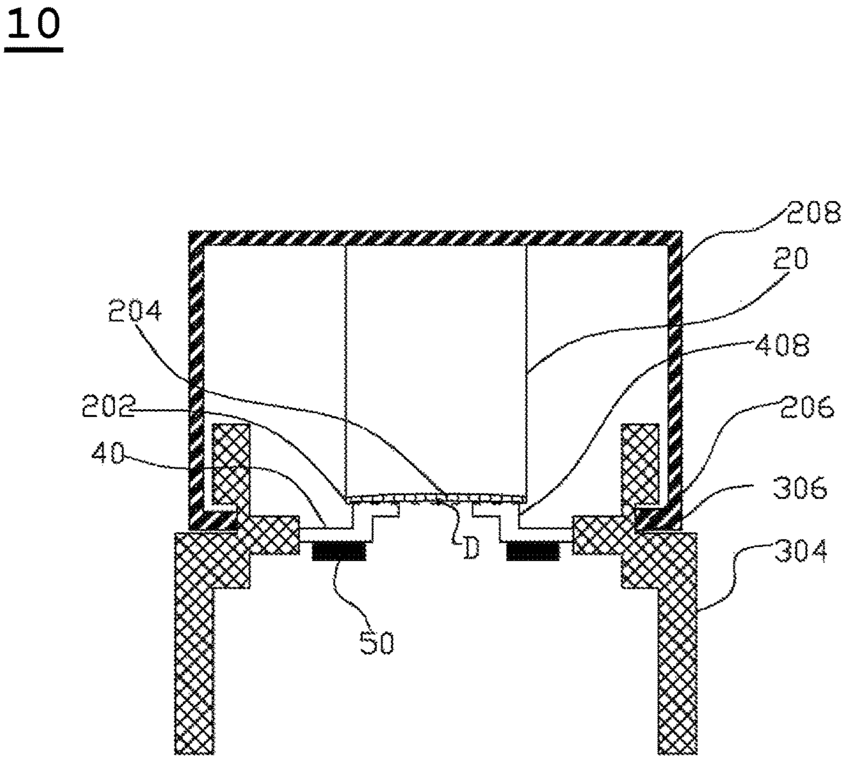

Referring to FIG. 5A, the aerosol generating apparatus 10 in the disengaged state is disclosed. A housing 208 for receiving the reservoir 20 is provided. The housing 208 further includes a first mating part 206 that corresponds to the second mating part 306 of the holder 30. In FIG. 5B, when the aerosol generating apparatus 10 is in the engaged state, the interaction between the first and second mating parts 206, 306 ensures that the membrane 202 is in contact with and/or pushed inward by the projection 408. In certain embodiments, there may be multiple second mating parts 306 at the holder 30 or the housing 304 in the form of a dial. Accordingly, when the aerosol generating apparatus 10 is in the engaged state, the user can adjust the distance D in which the membrane 202 is pushed inward by the projection 408 by coupling the first mating part 206 with different second mating parts (not shown). As such, aerosolization efficiency may be adjusted when the liquid medicament is about to deplete or power supply for the oscillation generator 50 is reduced.

Figure 5C:
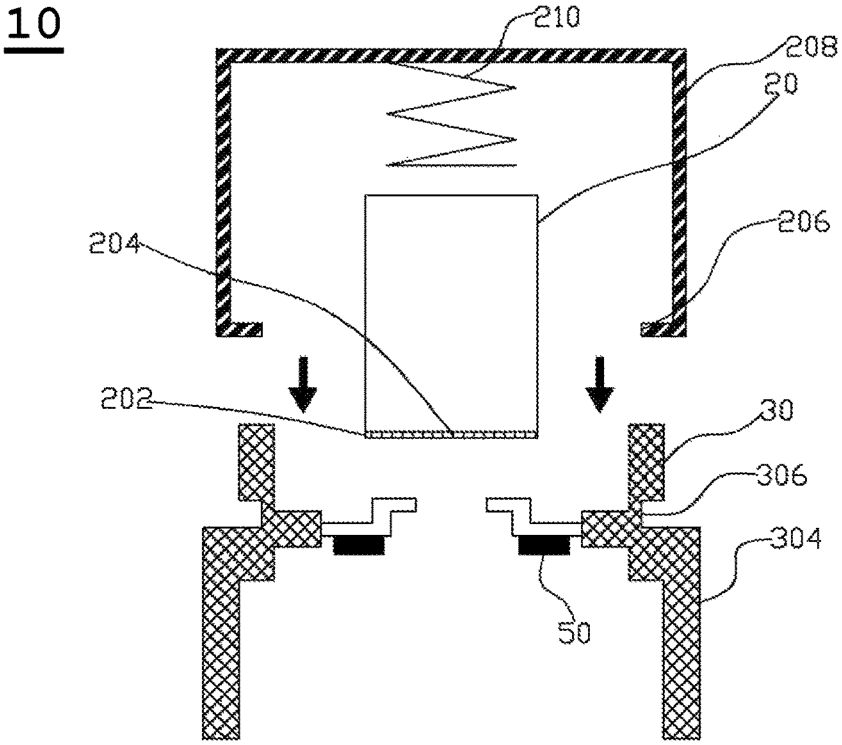
Figure 5D:
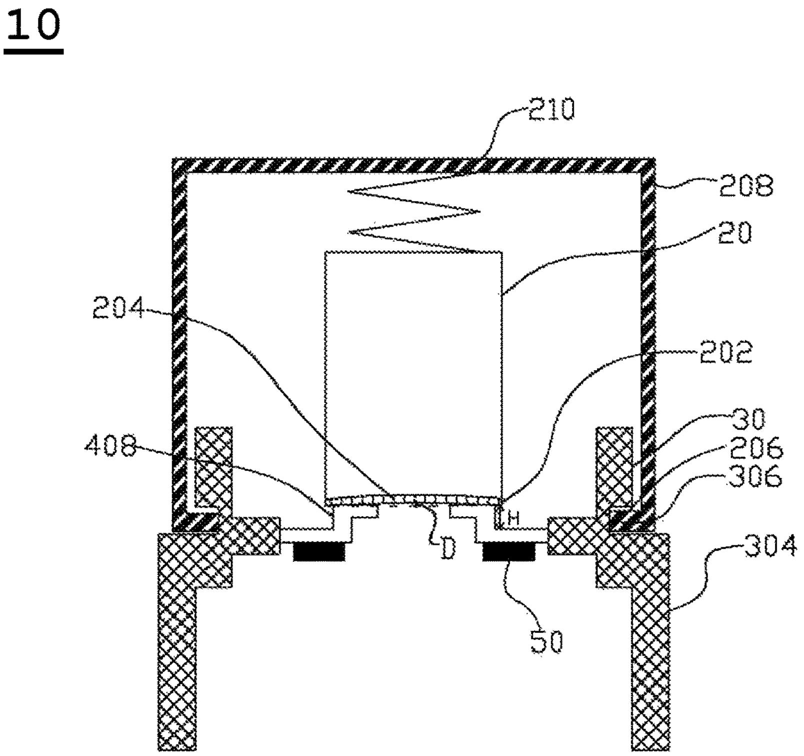

Referring to FIG. 5C, the aerosol generating apparatus 10 in the disengaged state is disclosed. The housing 208 includes a gear 210 for adjusting the distance D. In certain embodiments, the gear 210 is a spring pushing against the reservoir 20. Gear 210 may be of any material or structure readily contemplatable by persons having ordinary skill in the art if it is capable of providing a pushing force against the reservoir 20. For example, the gear may be a mass of elastic material or be made of a material capable of recovering from deformation/compression. With reference to FIG. 5D, when in the engaged state, the gear 210 pushes the reservoir 20 against the projection 408 to ensure that there is certain distance D. In combination with the first and second mating gears 206, 306, the distance D may be further adjusted.

Figure 5E:
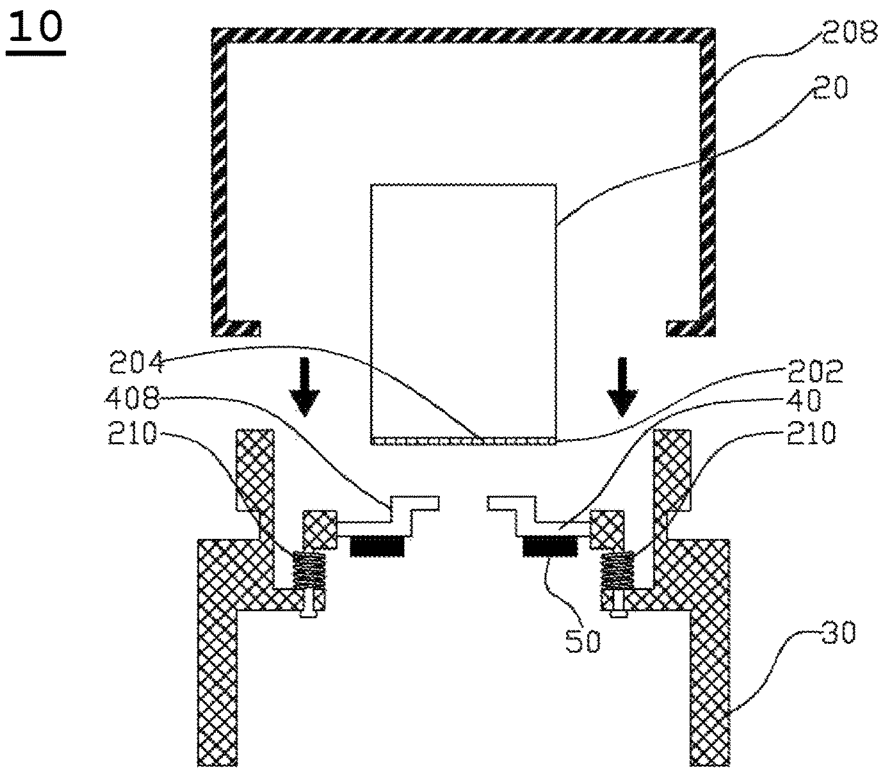
Figure 5F:
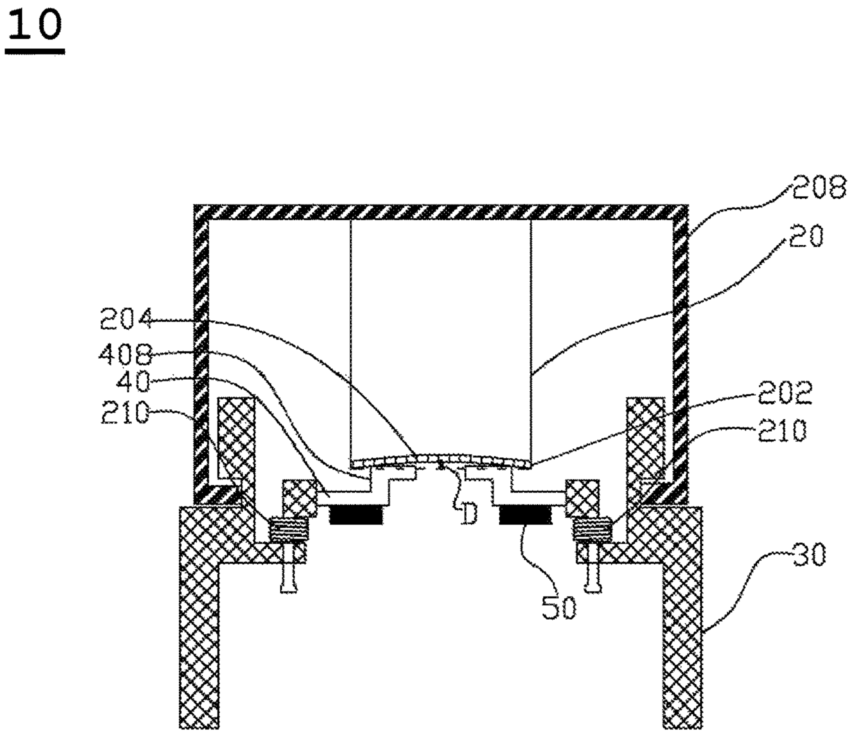

Referring to FIG. 5E, in some embodiments, one or more gear 210 is disposed at the holder 30 and configured to support the structure plate 40. In the disengaged state, the gear 210 is released and not compressed. In the engaged state, as depicted in FIG. 5F, the gear 210 is compressed. Reacting to the compression of the gear 210, the structure plate 40 and the projection 408 is pushed against the membrane 202 to form the distance D. The foregoing design may further be utilized to adjust the distance D in the engaged state. Alternatively, the gear 210 may be disposed in other locations of the holder 30 or the housing 304 if needed.

Figure 5G:
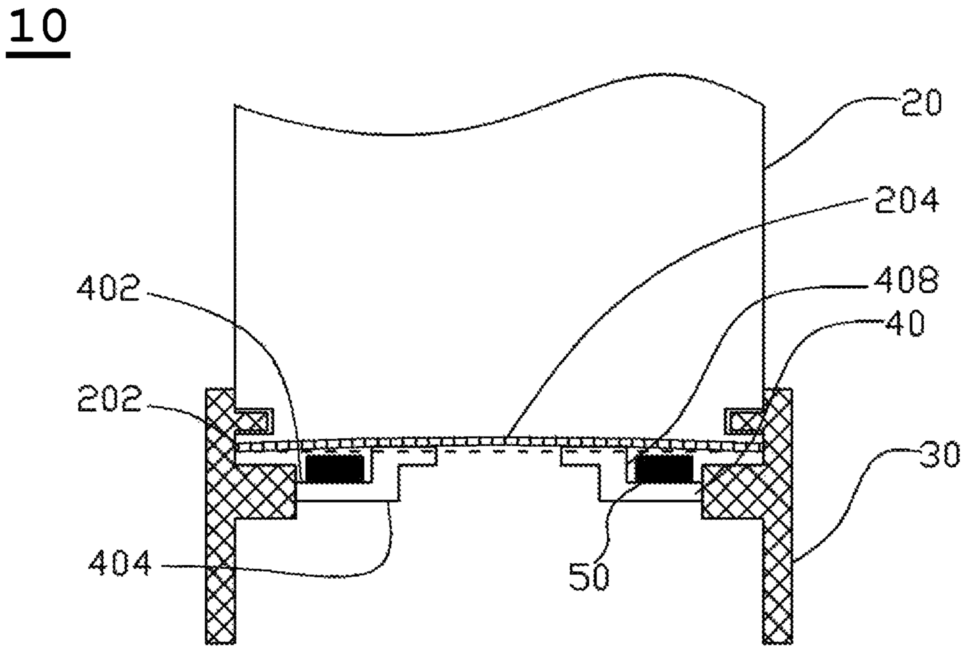

Referring to FIG. 5G, the aerosol generating apparatus 10 in the engaged state is disclosed. Rather than coupling to the outlet surface 404, the oscillation generator 50 is located at the inlet surface 402 of the structure plate 40. As such, the oscillation generator 50 is positioned between the membrane 202 and the structure plate 40. In certain embodiments, the height of the oscillation generator 50 is lower than the height H of the projection 408. Accordingly, the oscillation generator 50 is not in contact with the membrane 202 in the engaged state, and the vibration of the membrane 202 is not affected by the oscillation generator 50. However, the oscillation generator 50 may still touch the membrane 202 during aerosolization due to amplitude of vibration.

Figure 5H:
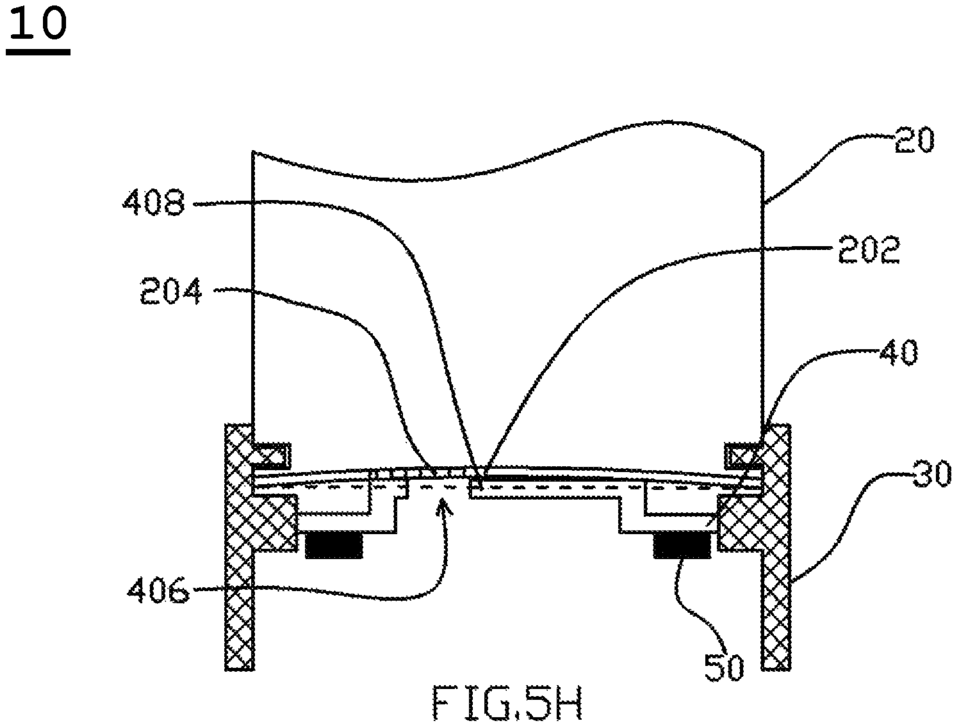

Referring to FIG. 5H, the aerosol generating apparatus 10 in the engaged state is disclosed. Here, the through hole 406 penetrates the projection 408 not around the center. In addition, the orifices 204 are distributed corresponding to the through hole 406. When the membrane 202 is vibrated by the projection 408, aerosol is generated and exits the structure plate 40 from the through hole 406. The foregoing embodiment may be suitable for specially designed aerosol generating apparatus. For example, the aerosol outlet may be tilted or curved to facilitate a patient's need.

In certain embodiments, the aerosol generating apparatus 10 may include two projections at the structure plate 40. Thus, more sections of the membrane 202 are pushed inward by such projections. Accordingly, when the oscillation generator 50 is in operation, more vibration energy may be transmitted to the membrane 202 via the projections and a different aerosolization pattern may be created. In certain embodiments, there might be more than one oscillation generator 50 coupled with the structure plate 40. The number of projections 408 is not limited to two and may be adjusted when needed, e.g., different types of liquid medicament or aerosolization cycle.

With reference to FIGS. 2A-5H, the dimension and material of the membrane 202, and the position and number of orifices 204 may be adjusted to meet different needs. For example, the size of the membrane 202 may be larger than, equal to, or smaller that of the projection 408 as long as only portion of the membrane 202 is in contact with the projection 408 while the rest of such membrane 202 is not. Moreover, the membrane 202 may cover either an entire side or only partial side of the reservoir 20. In certain embodiments, the orifices 204 may be distributed evenly over the entire membrane 202. Alternatively, the orifices 204 may be distributed according to the relative position of the projection 408 or the through hole 406 in the engaged state. Preferably, the location of the orifices 204 should not correspond exactly to the projection 408 or the through hole 406. That is, the orifices 204 may be distributed in areas larger or smaller than the projection 408 or the through hole 406. Alternatively, the orifices 204 may be distributed in any area of the membrane 202 because it's cheaper or easier to manufacture. In sum, the aerosol generating apparatus 10 in the present disclosure is capable of generating aerosol in a desired manner as long as only part of the membrane 202 is in contact with the projection 408, and vibration of the rest of the membrane 202 is not affected by the projection 408 or the structure plate 40.

FIGS. 6A to 6F are schematics of an aerosol generating apparatus with interchangeable parts in accordance with some embodiments of the present disclosure.

Figure 6A:
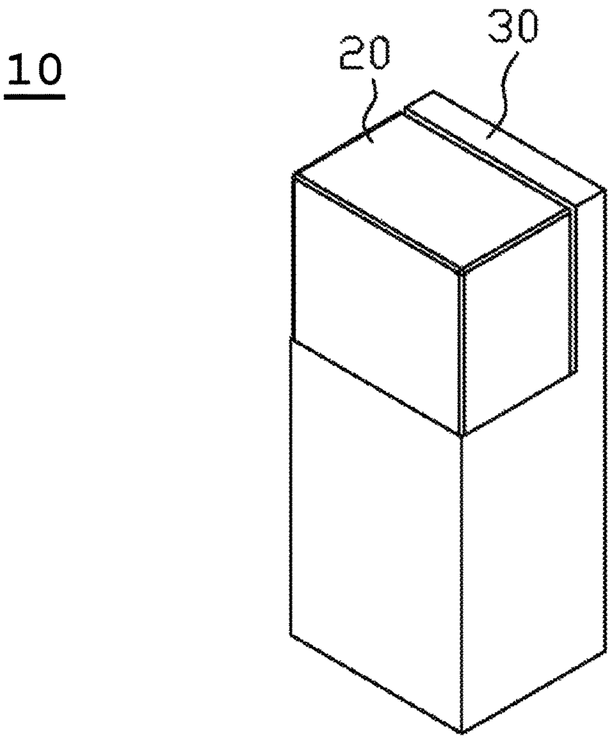
FIGS. 6A to 6F are schematics of an aerosol generating apparatus with interchangeable parts in accordance with some embodiments of the present disclosure.

FIG. 6A shows the aerosol generating apparatus 10 in an engaged state. During aerosolization, it is preferred that the reservoir 20 and the holder 30 are secured with respect to each other. In certain embodiments, the relative position of the reservoir 20 and the holder 30 is fixed during aerosolization. Alternatively, such relative position may be slightly shifted due to vibration. However, such slight shifting should not affect the engagement of the aerosol generating apparatus 10. Moreover, locking means as disclosed in FIGS. 6B to 6F may be applied to ensure that the reservoir 20 and the holder 30 are secured during aerosolization.

Figure 6B:
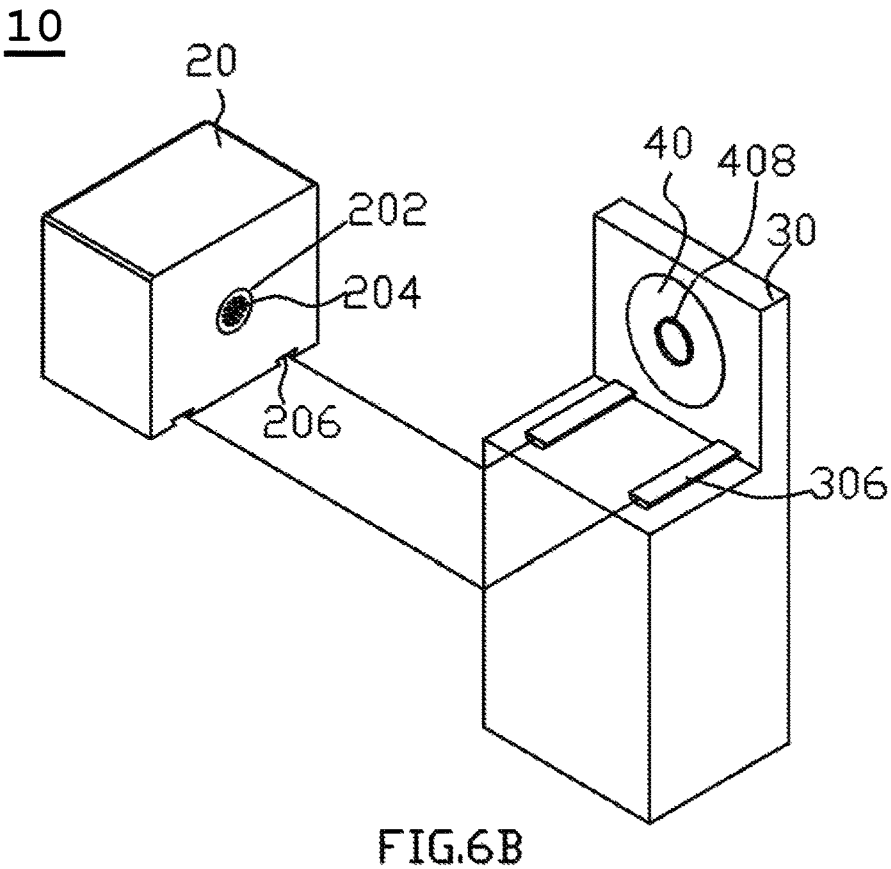

Referring the FIG. 6B, a slide locking means is provided. Here, the first mating part 206 is the groove of the slide and the second mating part 306 is the track of the slide. By coupling the reservoir 20 with the holder 30 along the slide, a user can easily engage two and have the membrane 202 contact the projection 408. Relative position of the reservoir 20 and the holder 30 can also be fixed during aerosolization.

Figure 6C:
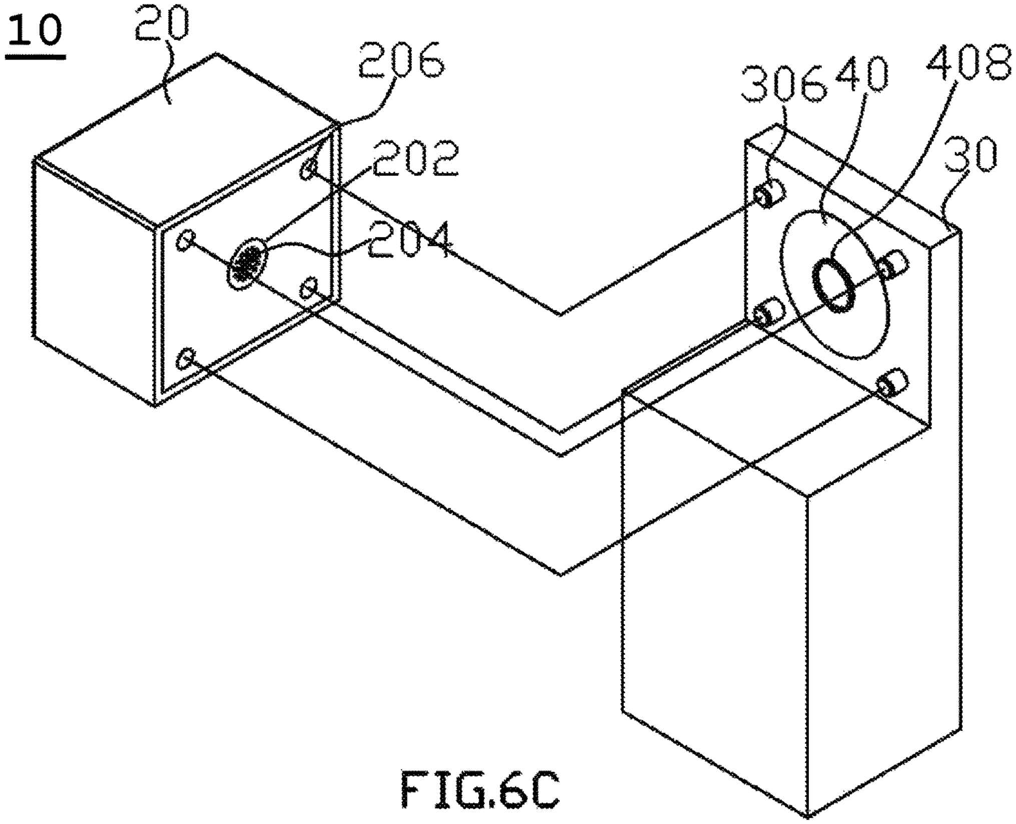

Referring to FIG. 6C, the first mating part 206 is in the form of a hole and the second mating part 306 is in the form of a shaft. Accordingly, the user can easily engage the reservoir 20 with the holder 30 by fitting the shafts and holes. In addition, when the first and second mating parts 206, 306 are mated, the membrane 202 is aligned with the projection 408. In certain embodiments, the structure of the first and second mating parts 206, 306 are interchangeable. Moreover, they might include magnetic material such that the reservoir 20 and the holder 30 can be magnetically engaged.

Figure 6D:
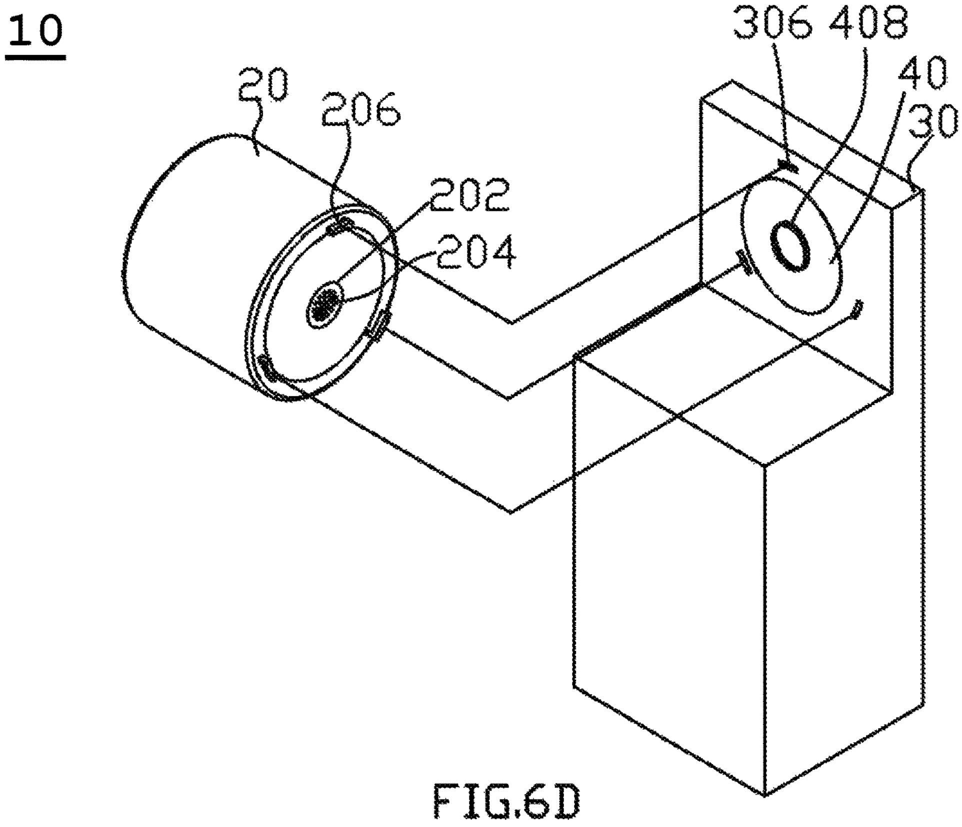

Referring to FIG. 6D, the first mating part 206 is in the form of an L-shaped projection and the second mating part 306 is in the form of an L-shaped recess. As such, after the first mating part 206 is fitted into the second mating part 306, the user may twist lock the two so as to mate the reservoir 20 with the holder 30. As a result, the relative position between the reservoir 20 and the holder 30 is fixed during aerosolization.

Figure 6E:
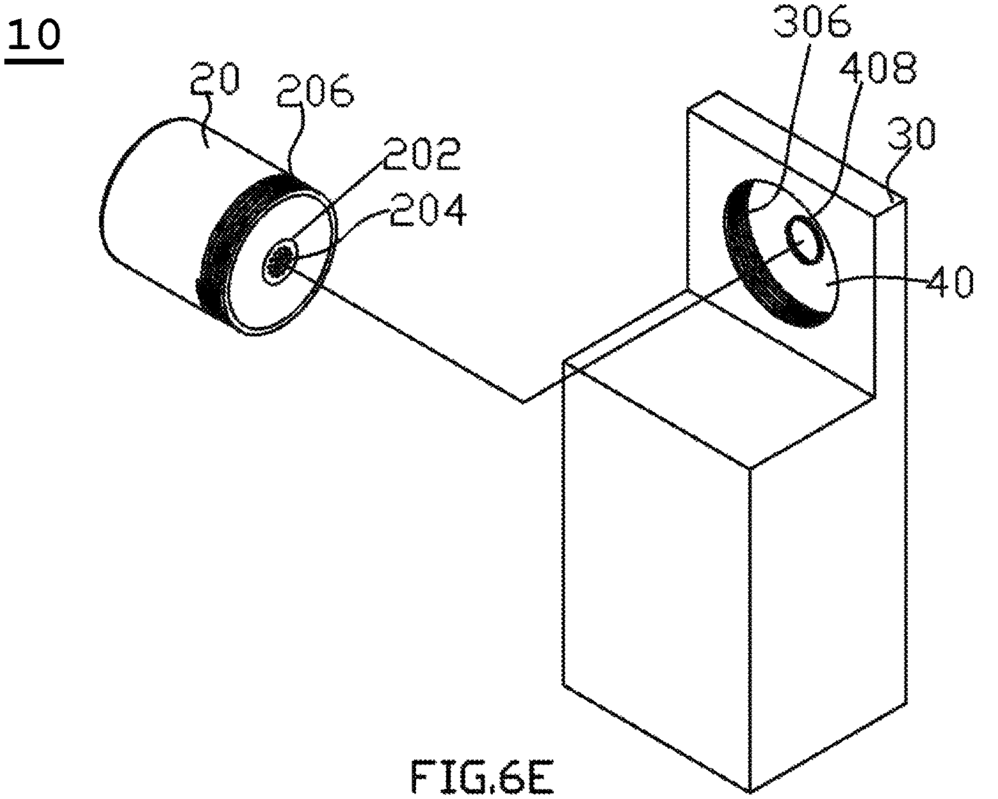

Referring to FIG. 6E, the first and second mating parts 206, 306 are correspondingly screw threaded. As such, the reservoir 20 and the holder 30 are engaged through screw lock, and the relative position thereof is fixed during aerosolization. The screw locking mechanism may also be utilized to adjust the extent in which the membrane 202 is pushed inward by the projection 408.

Figure 6F:
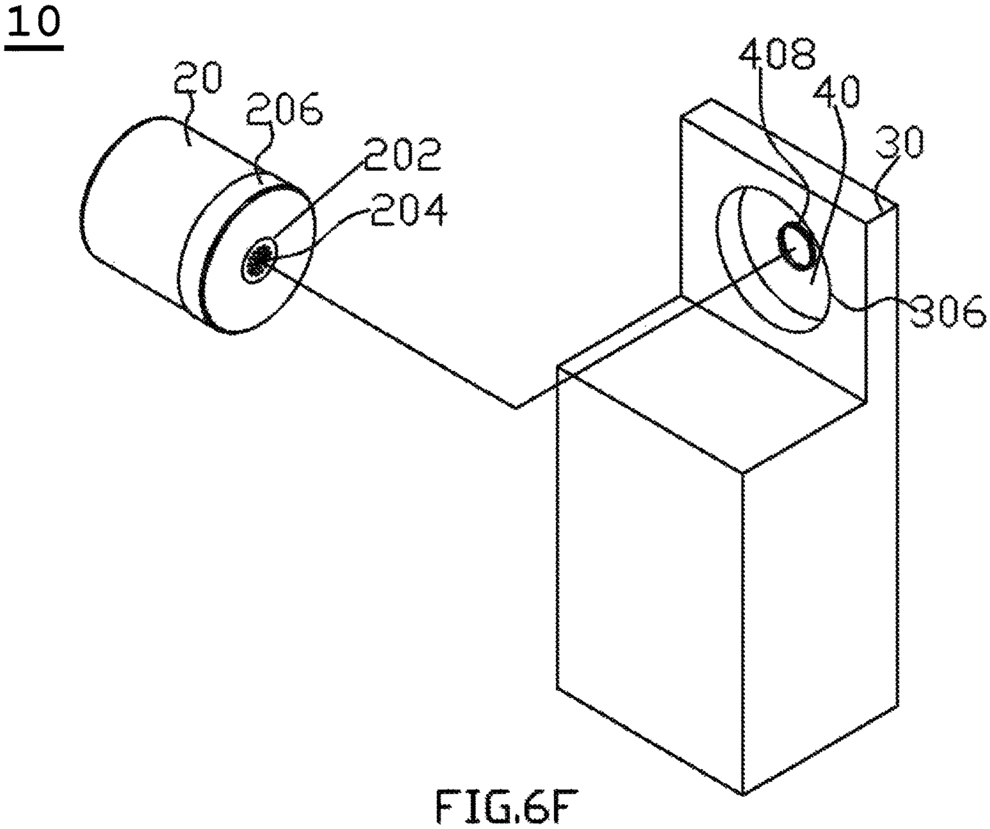

Referring to FIG. 6F, the second mating part 306 is an opening and the first mating part 206 is a flexible and/or malleable component, dimension of which is a bit larger than the second mating part 306. When engaged, user may apply force to fit the first mating part 206 into the second mating part 306. Because fitting of the first mating part 206 and second mating part 306 creates friction between the reservoir 20 and the holder 30, their relative position can be fixed.

With reference to FIGS. 6A-6F, in the present disclosure, at least one of the reservoir 20 and the holder 30 includes a locking means capable of repeated engagement and release. As a result, either the reservoir 20 or the holder 30 can be disengaged. In addition, the design of such locking means is simple to allow a user to engage and disengage the reservoir 20 and the holder 30 within two actions. An exemplary one action includes pulling, and an exemplary two action includes twisting and clicking. Thus, components of the present aerosol generating apparatus are readily separable and can be replaced with a new one easily. The foregoing is especially useful when a user is in urgent need to replace a malfunctioned aerosol generating apparatus. In some embodiments, the reservoir 20 and the holder 30 may be engaged by magnetic force. In yet some other embodiments, magnetic material may be mixed into the body of the reservoir 20 such that the entire reservoir 20 becomes magnetic. Thus, no additional components need to be added to the reservoir 20 for magnetic engagement.

FIGS. 7A to 7E are partial views of an aerosol generating apparatus with interchangeable parts in accordance with some embodiments of the present disclosure.

Figure 7A:
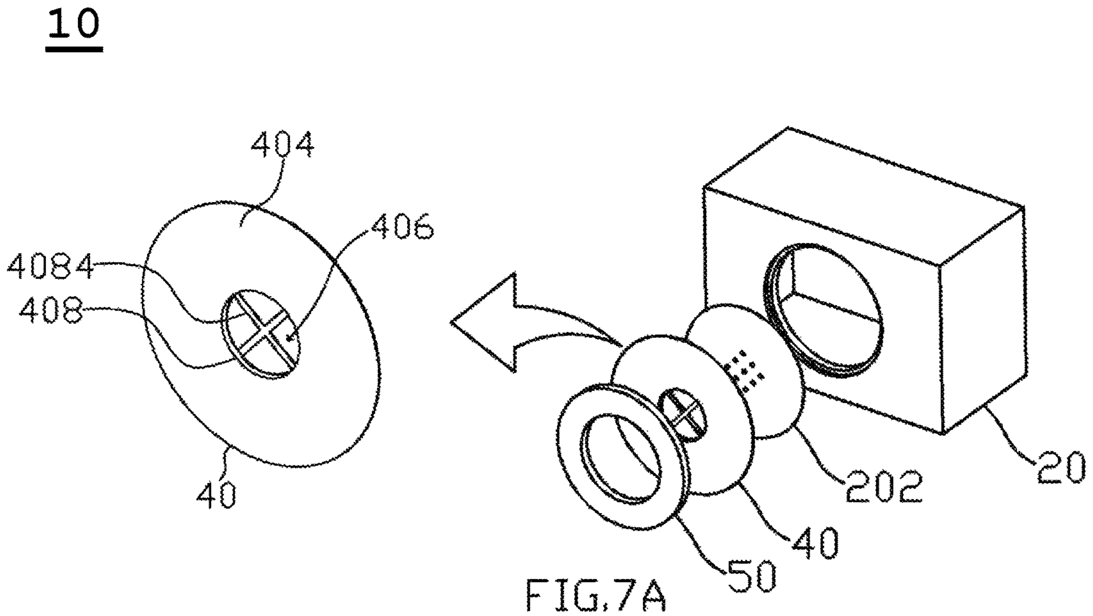
FIGS. 7A to 7E are partial views of an aerosol generating apparatus with interchangeable parts in accordance with some embodiments of the present disclosure.
Figure 7B:
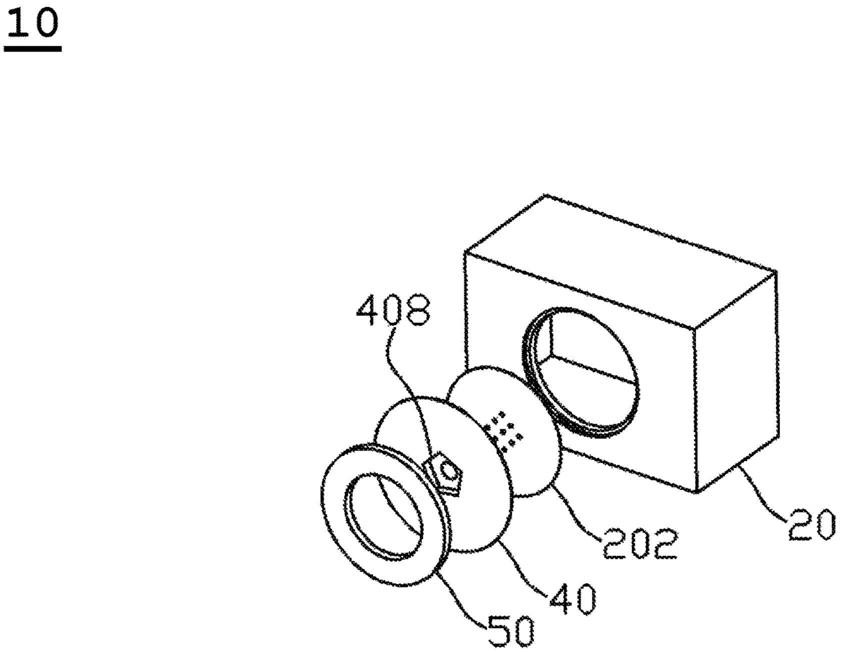
Figure 7C:
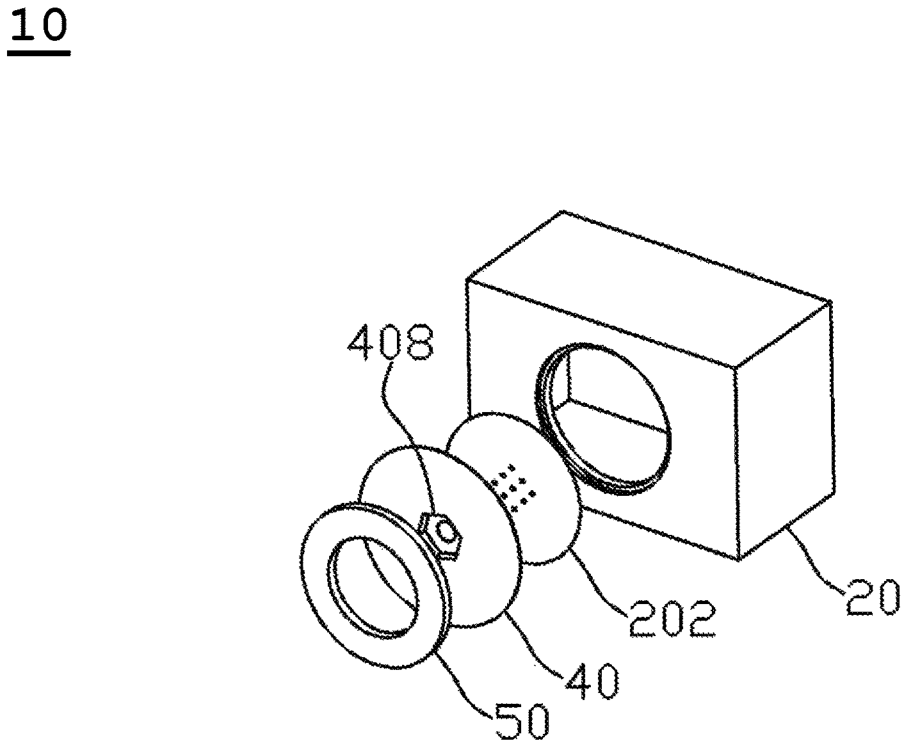
Figure 7D:
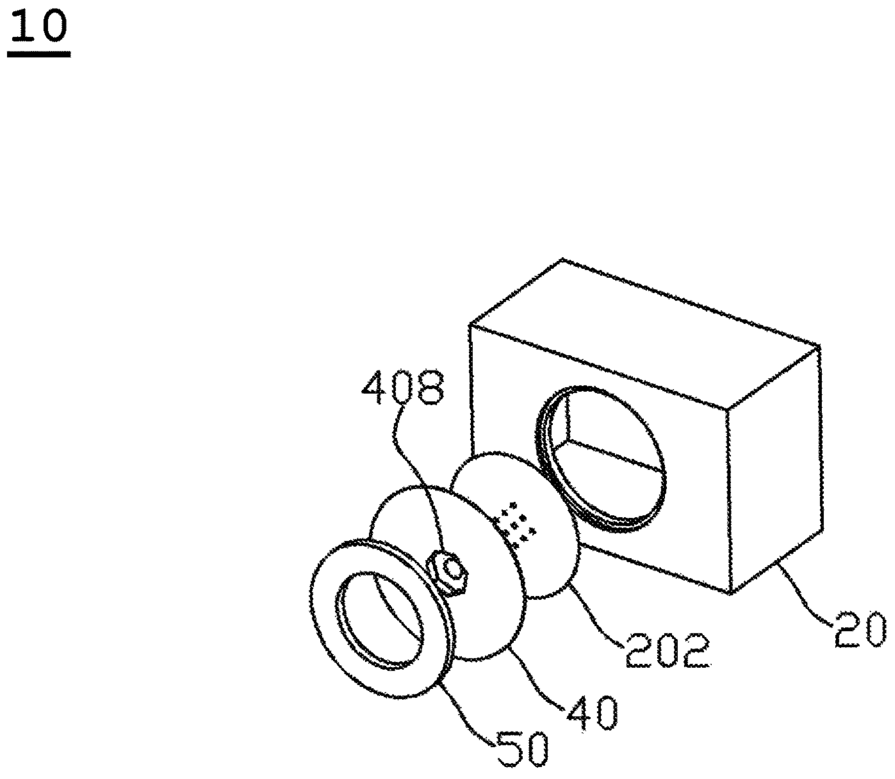
Figure 7E:
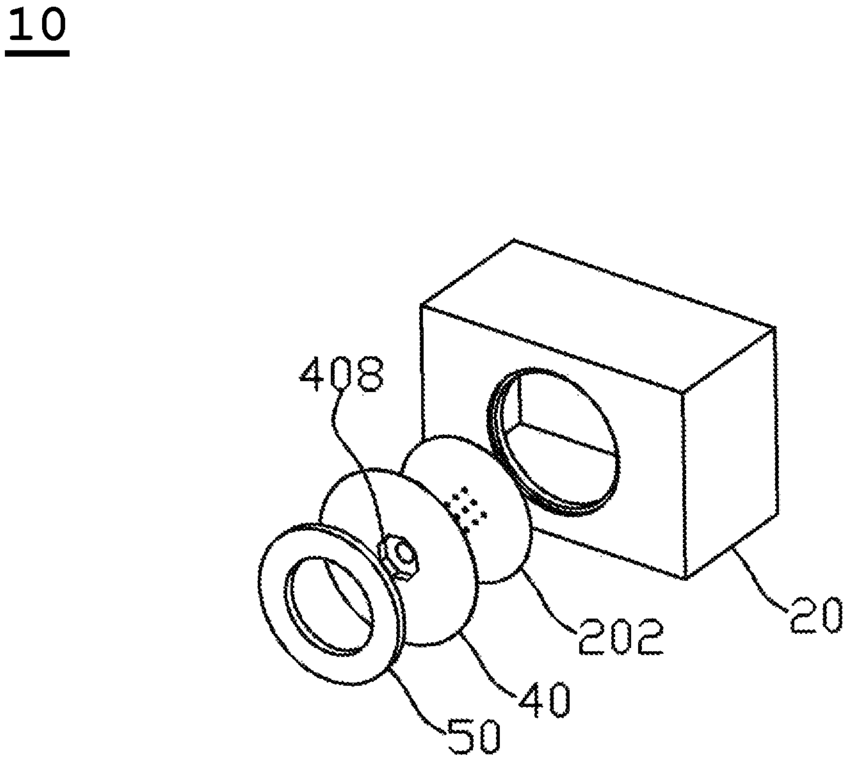

Referring to FIG. 7A, the aerosol generating apparatus 10 is shown and the structure plate 40 is enlarged for more clarity. In a preferred embodiment, the projection 408 extending from the face of the inlet surface 402 of the structure plate 40 is circular. Corresponding stress concentration points are formed at the membrane 202 when the aerosol generating apparatus 10 is in the engaged state. The formation of the stress concentration points may improve the aerosolization efficiency as vibration energy may be directed to certain points or areas of the membrane 202 where the orifices 204 are located or where vibration of the membrane 202 is maximized. For example, vibration energy may be directed towards the center of the membrane 202 and thus oscillation amplitude thereof is the highest comparing to other sections of the membrane 202. Alternatively, the stress concentration points help the membrane 202 to achieve a resonance state. In certain embodiments, the projection 408 includes at least one rib 4084 across the through hole 406. When the aerosol generating apparatus 10 is in the engaged state, the rib 4084 is in contact with the membrane 202 such that more stress concentration points may be formed. As a result, the aerosolization efficiency of the aerosol generating apparatus 10 may be further adjusted.

The shape of the projection 408 is not limited to circular. In certain embodiments, the projection 408 is of a polygonal shape with three or more edges. For example, projection 408 in the shape of a pentagon, hexagon, heptagon or octagon is illustrated in FIGS. 7B through 7E. Based on the different distribution of stress concentration points formed by different shapes of projection 408 and the vibration frequency applied, the corresponding aerosolization efficiency may vary. For example, in some embodiments, when provided with a vibration frequency of about 100 to 150 KHz, the aerosolization efficiency of the present aerosol generating apparatus is between about 0.2 and 0.9 ml/min, the difference of which may be caused by the different combination of shape, number, diameter or height of the projection 408, or vibration frequency provided, vibration modes or nodes of the membrane 202 and/or the oscillation generator 50. A preferred aerosolization efficiency of the present disclosure is more than about 0.2 ml/min.

Figures 8A, 8B:
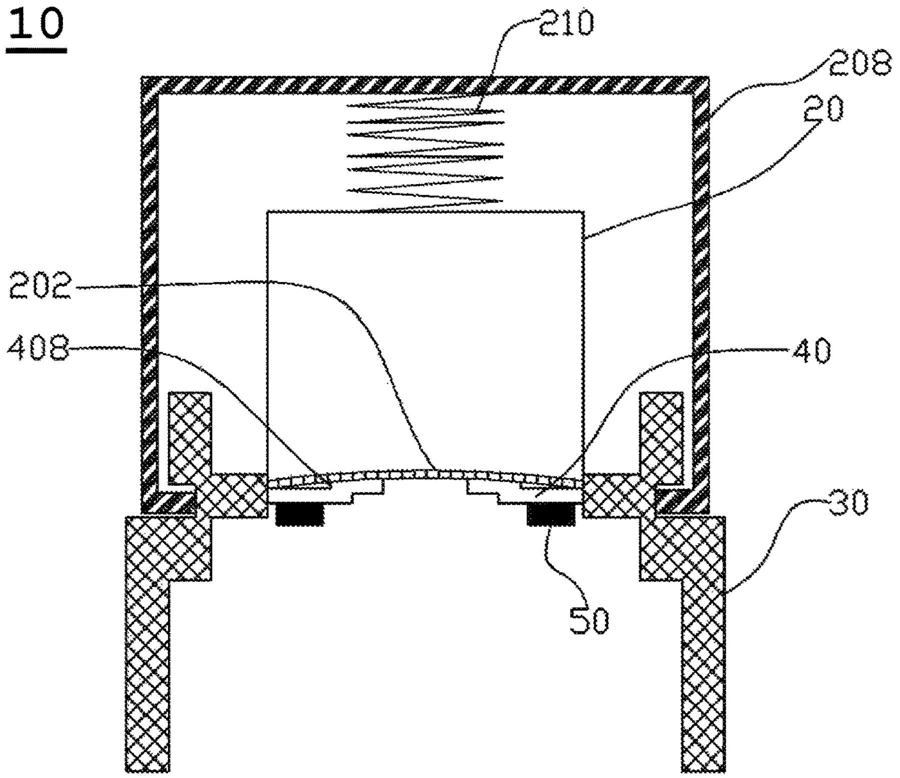
FIG. 8A is a perspective view of an aerosol generating apparatus with interchangeable parts in accordance with some embodiments of the present disclosure.
FIG. 8B is a diagram of aerosolization efficiency of an aerosol generating apparatus with interchangeable parts in accordance with some embodiments of the present disclosure.

FIG. 8A is a perspective view of an aerosol generating apparatus with interchangeable parts in accordance with some embodiments of the present disclosure. FIG. 8B is a diagram of aerosolization efficiency of an aerosol generating apparatus with interchangeable parts in accordance with some embodiments of the present disclosure.

As disclosed herein, in a preferred embodiment, the height H of the projection 408 is at least 0.1 mm such that free-form movement of those sections of the membrane 202 not affected by the structure plate 40 and/or the projection 408 is preserved. Specifically, when the projection 408 has a height H of only 0.1 mm, any contact more than a mere touch with the membrane 202 would cause the space 410 between the membrane 202 and the structure plate 40 to become factually non-existent, thereby dropping the aerosolization efficiency to a minimally detectable level. This is because the membrane 202 cannot enter into a resonance state for aerosolization without the space 410. In other words, the preferred embodiment of the present invention comprises a projection 408 having a height of at least 0.1 mm because it is the minimal height required to create the space 410 when the projection 408 touches the membrane 202. FIG. 8A shows that when the height H is less than 0.1 mm, the movement of the membrane 202 will be affected by the structure plate 40 directly if the membrane 202 is not merely in contact with the projection 408, which results in a poor aerosolization efficiency. The foregoing can be supported by the diagram in FIG. 8B, which shows the aerosolization efficiencies when the height H is less than 0.1 mm and more than 0.1 mm (we use 0.2 mm for comparison here). When the height H is less than 0.1 mm, the aerosolization efficiency is always below 0.1 ml/min. On the other hand, when the height H is 0.2 mm, the aerosolization efficiency generally reaches more than 0.3 ml/min. As previously disclosed, the present aerosol generating apparatus preferably conveys an aerosolization efficiency more than about 0.2 ml/min. As such, the height H is preferably no less than 0.1 mm.

Figure 9A:
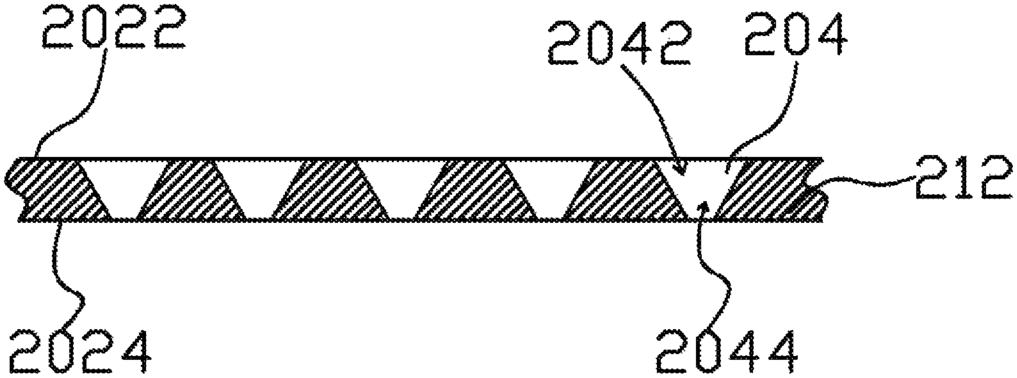
FIGS. 9A and 9B are partial views of the membrane of an aerosol generating apparatus with interchangeable parts in accordance with some embodiments of the present disclosure.
Figure 9B:
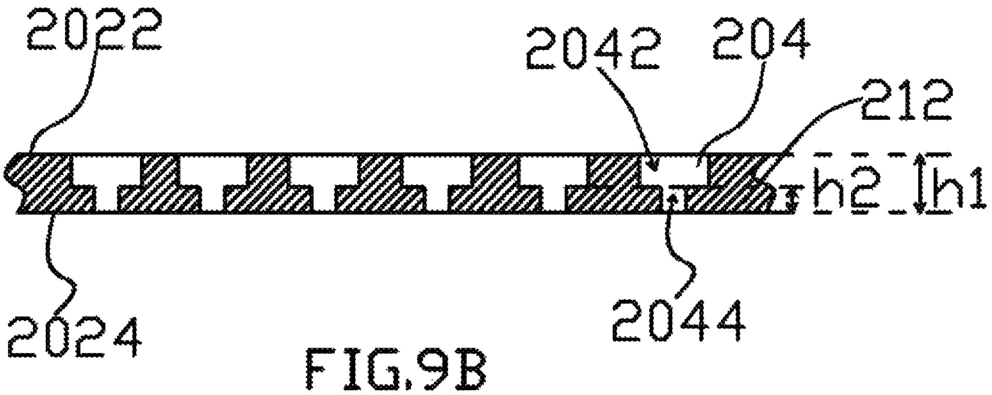

FIGS. 9A and 9B are partial views of the membrane of an aerosol generating apparatus with interchangeable parts in accordance with some embodiments of the present disclosure.

In FIG. 9A, the membrane 202 and the orifices 204 penetrating thereof are disclosed. Particularly, the membrane 202 includes an inlet surface 2022 and an outlet surface 2024. During aerosolization, the liquid medicament enters the membrane 202 from the inlet surface 2022 and exits from the outlet surface 2024. In some embodiments, the entrance and the exit of the orifice are of the same size. In certain embodiments, as depicted in FIG. 9A, the entrance 2042 is larger than the exit 2044 of the orifice 204. In other words, the orifice 204 narrows in the direction from the inlet surface 2022 to the outlet surface 2024 and is tapered. Such configuration may help to improve aerosolization efficiency. The orifice 204 may be continuously narrowing in the direction from the inlet surface 2022 to the outlet surface 2024. Alternatively, with reference to FIG. 9B, the orifice 204 may not be continuously narrowing in the direction from the inlet surface 2022 to the outlet surface 2024, and a stepped structure is formed.

Referring to FIG. 9B, the stepped orifice 204 has an orifice height h1, and a nozzle height h2. The orifice height h1 is essentially the thickness of the membrane 202. The nozzle height h2 is defined as the depth of the narrowest part (the nozzle part) of the orifice 204, which is in connection with the exit 2044. The orifice 204 with the combination of orifice height h1 and nozzle height h2, i.e., with a stepped structure, helps to improve aerosolization efficiency. The orifice 204 may include more than one step, and there may be more than one nozzle parts at each orifice 204.

Figure 10A:
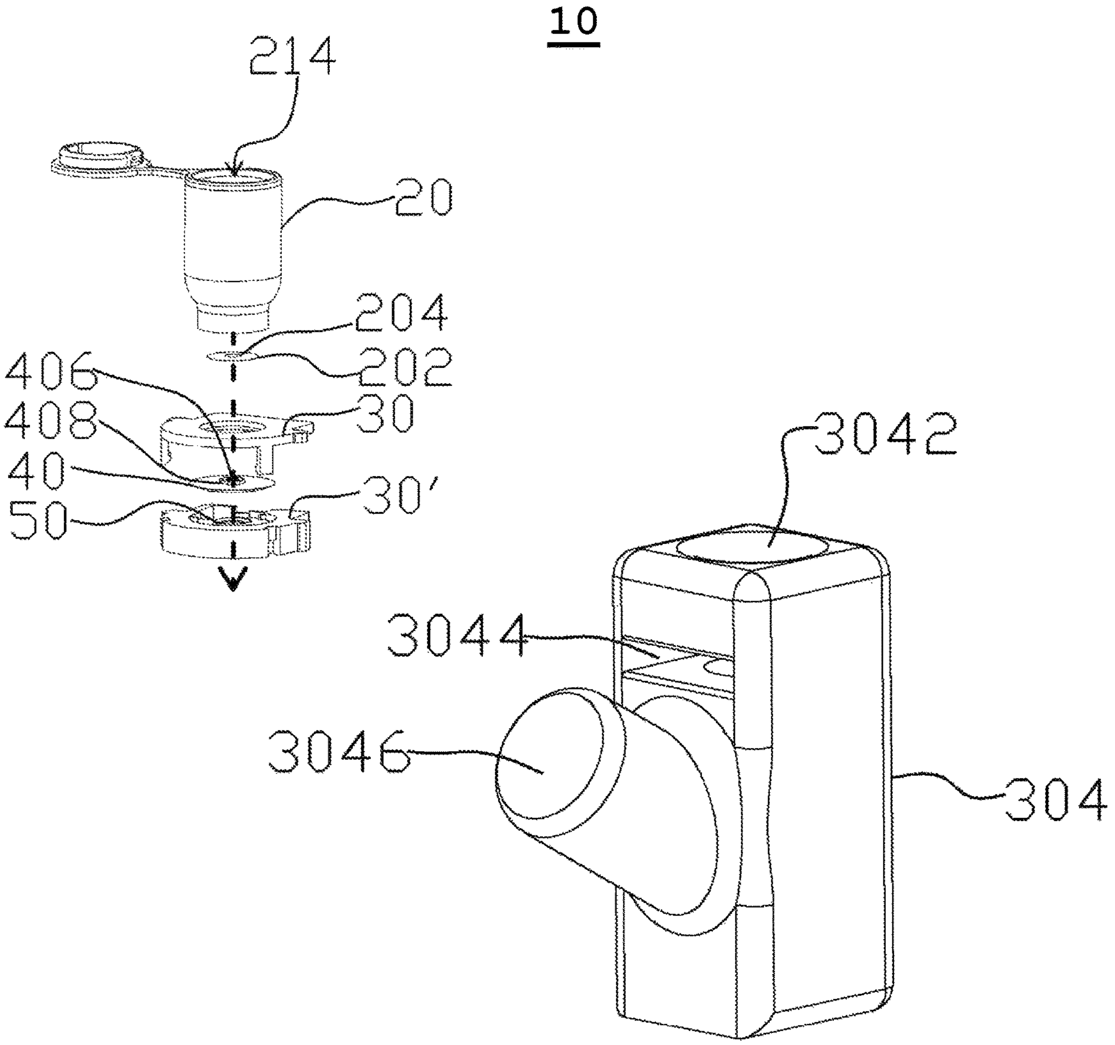
FIGS. 10A and 10B are some preferred embodiments of the aerosol generating apparatus with interchangeable parts of the present disclosure.
Figure 10B:
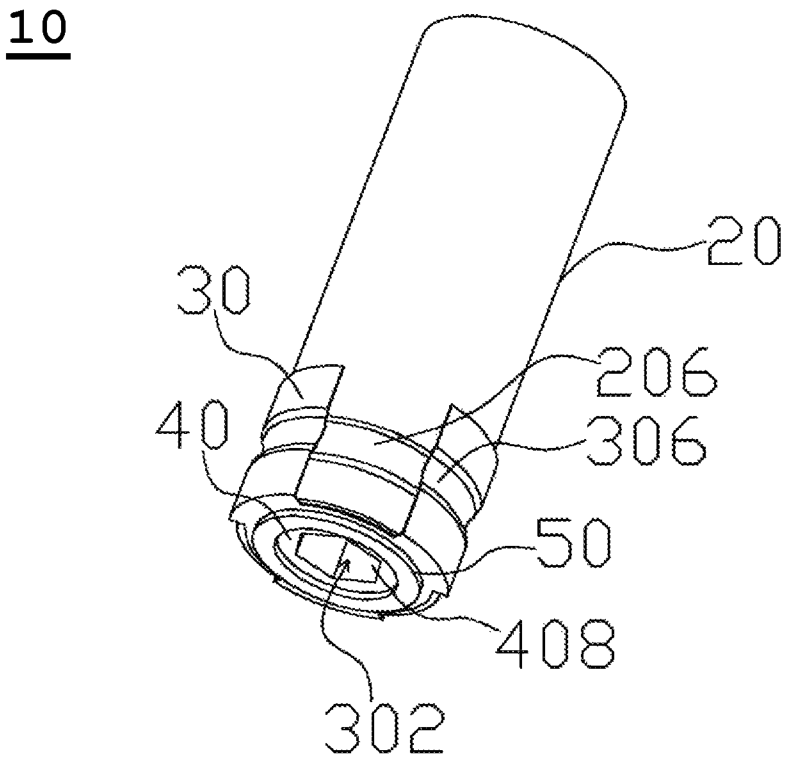

FIGS. 10A and 10B are some preferred embodiments of the aerosol generating apparatus with interchangeable parts of the present disclosure.

FIG. 10A is a partially exploded figure of the aerosol generating apparatus 10 in accordance to some embodiments of the present disclosure. The reservoir 20 includes an opening 214 for liquid medicament (not shown) refill. The membrane 202 is disposed at one side of the reservoir 20. The orifices 204 of the membrane 202 is distributed corresponding to the projection 408 of the structure plate 40. The structure plate 40 and the oscillation generator 50 is accommodated by one or more holders 30, 30'. When in the engaged state, the oscillation generator 50 is in contact with the structure plate 40, and the projection 408 is in contact with the membrane 202. When provided with electric power, the oscillation generator 50 vibrates. The resulting vibration energy is transmitted to the membrane 202 through the projection 408 of the structure plate 40. Accordingly, liquid medicament aerosolizes and ejects in the direction of the dotted arrow as depicted in FIG. 10A. In certain embodiments, the aerosol generating apparatus 10 includes a housing 304 for receiving its components. For example, the reservoir 20 can be received by compartment 3042, and the holder 30 and the structure plate 40 and oscillation generator 50 accommodated therein can be received by compartment 3044. Thus, during aerosolization, aerosol is created and exits the housing 304 via the opening 3046. A patient can breathe directly through the opening 3046. Alternatively, the opening 3046 may be part of a mouthpiece, or a conveying tube (not shown) may be connected to the opening 3046 if needed.

FIG. 10B depicts another preferred embodiment of the aerosol generating apparatus of the present disclosure. Here, the holder 30 includes a second mating part 306 that engages with the first mating part 206 (e.g., a groove) of the reservoir 20. Thus, the reservoir 20 is engaged with the holder 30. As depicted, in the engaged state, the projection 408 pushes the membrane (obstructed, not shown) inward. Vibration energy from the oscillation generator 50 is transmitted to the membrane (obstructed, not shown) through the projection 408 of the structure plate 40. As a result, aerosol of the liquid medicament exits the aerosol generating apparatus 10 via the opening 302.

The present disclosure provides an aerosol generating apparatus with interchangeable parts. Particularly, a reservoir is detachably engaged with a holder, which includes a structure plate and an oscillation generator. The reservoir includes a membrane facing a projection of the structure plate. The projection and the membrane may have different states of interaction when the reservoir is engaged with the holder. In some embodiments, the membrane is in contact with the projection without being deformed. In certain embodiments, the membrane is pushed inward by the projection such that some deformation occurs. Vibration energy generated by the oscillation generator is transmitted to the membrane via the projection. By adjusting the state of interaction between the membrane and the projection, aerosolization can be controlled. The foregoing is achieved due to the detachable nature of the present aerosol generating apparatus. In addition, the readily exchangeable reservoir and the holder (and the structure plate and an oscillation generator accommodated therein) helps to further improve aerosolization efficiency and avoid waste.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

LISTING OF ELEMENTS

10 aerosol generating apparatus
20 reservoir
202 membrane
2022 inlet surface
2024 outlet surface
204 orifice
2042 entrance
2044 exit
206 first mating part
208 housing
210 gear
212 liquid medicament
214 opening
30 holder
302 opening
304 housing
3042 compartment
3044 compartment
3046 opening
306 second mating part
40 structure plate
402 inlet surface
404 outlet surface
406 through hole
408 projection
4082 working surface
4084 rib
410 space
412 planar part
50 oscillation generator
D distance
H height
h1 orifice height
h2 nozzle height

What is claimed is:

1. An aerosol generating apparatus comprising:

a holder for accommodating a structure plate and an oscillation generator, wherein the structure plate includes an inlet surface, an outlet surface, a projection extending from the face of the inlet surface, and a through hole wherein the through hole penetrates the structure plate, and the oscillation generator couples with and vibrates the structure plate; and a reservoir for providing a liquid medicament, the reservoir is detachably engaged with the holder and includes a membrane with a plurality of orifices through which the liquid medicament passes during aerosolization, wherein when the reservoir is engaged with the holder, the membrane of the reservoir is in contact with the projection extending from the face of the inlet surface, wherein the oscillation generator vibrates the membrane through the projection on the inlet surface such that the membrane is capable of free-form movement and the liquid medicament aerosolizes and ejects via the outlet surface of the structure plate, wherein the membrane is made of a macromolecular polymer selected from the collection of polyimide, polyethylene (PE), polypropylene (PP) and polyether ether ketone (PEEK), wherein a height of the projection is no less than 0.1 mm.

2. The aerosol generating apparatus according to claim 1, wherein when the reservoir is engaged with the holder, the projection extending from the face of the inlet surface pushes the membrane inward for a distance, wherein the distance is less than or equal to the height of the projection.

3. The aerosol generating apparatus according to claim 2, further comprising a gear to adjust the distance in which the membrane is being pushed inward by the projection when the reservoir is engaged with the holder.

4. The aerosol generating apparatus according to claim 2, wherein a space between the inlet surface and the membrane is formed when the projection pushes the membrane inward.

5. The aerosol generating apparatus according to claim 4, wherein the structure plate further includes a planar part at the inlet surface extending annularly from the projection, and the space corresponds to the planar part.

6. The aerosol generating apparatus according to claim 1, wherein the reservoir is disengaged from the holder and replaced by another reservoir after an aerosolization cycle.

7. The aerosol generating apparatus according to claim 1, wherein the structure plate further includes a planar part at the inlet surface and extending annularly from the projection, and when the reservoir is engaged with the holder, vibration of the membrane is not affected by the planar part.

8. The aerosol generating apparatus according to claim 1, wherein at least one of the holder and the reservoir includes a locking means capable of repeated engagement and release.

9. The aerosol generating apparatus according to claim 1, wherein the plurality of orifices is aligned with a center of the projection extending from the face of the inlet surface when the reservoir is engaged with the holder.

10. The aerosol generating apparatus according to claim 1, wherein the membrane is in direct contact with the projection extending from the face of the inlet surface when the reservoir is engaged with the holder.

11. The aerosol generating apparatus according to claim 1, wherein the projection further comprises a working surface dimension of which not larger than that of the membrane, and the working surface faces the membrane and serves as a primary interface for transmitting vibration to the membrane when the projection is in contact with the membrane.

12. The aerosol generating apparatus according to claim 1, wherein the structure plate includes a planar part at the inlet surface and extending annularly from the projection, wherein the planar part is not sealed by the membrane when the reservoir is engaged with the holder.

13. The aerosol generating apparatus according to claim 1, wherein the projection is circular or of a polygonal shape with three or more edges.

14. The aerosol generating apparatus according to claim 1, wherein the oscillation generator is at the outlet surface side of the structure plate.

15. An aerosol generating apparatus comprising:

a holder for accommodating a structure plate and an oscillation generator, wherein the structure plate includes an inlet surface, an outlet surface, a projection extending from the face of the inlet surface, and a through hole wherein the through hole penetrates the structure plate, and the oscillation generator couples with and vibrates the structure plate; and a reservoir for providing a medicament, the reservoir is detachably engaged with the holder and includes a membrane with a plurality of orifices through which the medicament passes during aerosolization, wherein when the reservoir is engaged with the holder, the membrane of the reservoir is in contact with the projection extending from the face of the inlet surface, wherein the oscillation generator vibrates the membrane through the projection on the inlet surface such that the medicament aerosolizes and ejects via the outlet surface of the structure plate, wherein the projection includes a wall substantially perpendicular to the inlet surface and a top surface substantially parallel to the inlet surface extending inwardly beyond the wall towards a center of the projection for a length, wherein portion of the top surface in contact with the membrane is a working surface for transmitting vibration from the oscillation generator to the membrane.

16. The aerosol generating apparatus according to claim 15, wherein when the reservoir is engaged with the holder, the projection extending from the face of the inlet surface pushes the membrane inward for a distance, and size of the working surface is adjustable corresponding to the distance.

17. The aerosol generating apparatus according to claim 15, wherein a height of the projection is no less than 0.1 mm.

18. An aerosol generating apparatus comprising:

a holder for accommodating a structure plate and an oscillation generator, wherein the structure plate includes an inlet surface, an outlet surface, a projection extending from the face of the inlet surface, and a through hole wherein the through hole penetrates the structure plate, and the oscillation generator couples with and vibrates the structure plate; and a reservoir for providing a substance, the reservoir is detachably engaged with the holder and includes a membrane with a plurality of orifices through which the substance passes during aerosolization, wherein when the reservoir is engaged with the holder, the membrane of the reservoir is in contact with the projection extending from the face of the inlet surface, wherein the oscillation generator vibrates the membrane through the projection such that vibration energy of the oscillation generator travels in a radially inward manner to a central region of the membrane where oscillation amplitude thereof is the highest comparing to other regions of the membrane, and the substance proximate to the central region of the membrane ejects via the outlet surface of the structure plate, wherein the membrane is made of a macromolecular polymer selected from the collection of polyimide, polyethylene (PE), polypropylene (PP) and polyether ether ketone (PEEK), wherein a height of the projection is no less than 0.1 mm.

19. The aerosol generating apparatus according to claim 18, wherein the plurality of orifices are concentrated at or near the central region of the membrane.

* * * * *